United States Patent
Shelton, IV et al.

(10) Patent No.: US 12,164,985 B1
(45) Date of Patent: Dec. 10, 2024

(54) SYSTEM AND METHOD FOR SELECTIVELY ADJUSTABLE DATA EXCHANGE BETWEEN A SMART PACKAGE AND A REQUESTING SYSTEM

(71) Applicant: Cilag GmbH International, Zug (CH)

(72) Inventors: Frederick E. Shelton, IV, Cincinnati, OH (US); Jacqueline C. Aronhalt, Loveland, OH (US); Kevin M. Fiebig, Cincinnati, OH (US); Matthew D. Cowperthwait, Cincinnati, OH (US); Shane R. Adams, Cincinnati, OH (US); Taylor W. Aronhalt, Loveland, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/226,505

(22) Filed: Jul. 26, 2023

Related U.S. Application Data

(60) Provisional application No. 63/525,572, filed on Jul. 7, 2023.

(51) Int. Cl.
  *G06K 7/10* (2006.01)
  *G06K 17/00* (2006.01)
  *G06K 19/077* (2006.01)

(52) U.S. Cl.
  CPC ..... *G06K 17/0029* (2013.01); *G06K 7/10099* (2013.01); *G06K 19/07749* (2013.01)

(58) Field of Classification Search
  CPC ........... G06K 17/0029; G06K 7/10099; G06K 19/07749
  See application file for complete search history.

(56) References Cited

U.S. PATENT DOCUMENTS

| | | |
|---|---|---|
| 6,428,867 B1 | 8/2002 | Scott et al. |
| 6,861,954 B2 | 3/2005 | Levin |

(Continued)

FOREIGN PATENT DOCUMENTS

| | | | | |
|---|---|---|---|---|
| CA | 2593679 A1 | * | 12/2008 | ............ A61M 5/007 |
| CA | 2725727 A1 | * | 12/2009 | ............ A61B 90/90 |

(Continued)

OTHER PUBLICATIONS

JP 2008171446A—System and Method for Managing Information Relating To Medical Fluid and Container Therefor, 36 pages. (Year: 2024).*

(Continued)

*Primary Examiner* — Tuyen K Vo
(74) *Attorney, Agent, or Firm* — Condo Roccia Koptiw LLP

(57) ABSTRACT

Systems, methods, and devices for selectively adjustable data exchange are provided. In an aspect, an assembly including a protective container having a medical device disposed therein is provided. The protective container can be sealed to prevent contaminates from contacting the medical device. The assembly can further include a radiofrequency identification (RFID) tag disposed within the protective container. The RFID can include a data processor and memory storing first data and instructions configured to cause the data processor to perform operations. The operations can include receiving request data from a remote network in operable communication with the RFID. The request data can characterize a future data processing operation to be performed on a subset of the first data after the subset is transmitted from the RFID tag and a request for the subset of the first data to be transmitted from the RFID tag to the remote network. The operations can include determining the subset of the first data to be provided to the (Continued)

remote network. The operations can further include providing the determined subset of the first data to the remote network.

17 Claims, 9 Drawing Sheets

(56) References Cited

U.S. PATENT DOCUMENTS

| | | | |
|---|---|---|---|
| 7,256,696 | B2 | 8/2007 | Levin |
| 7,738,971 | B2 | 6/2010 | Swayze et al. |
| 8,248,232 | B2 * | 8/2012 | Stevenson .............. A61B 90/98 |
| | | | 343/873 |
| 8,253,555 | B2 * | 8/2012 | Stevenson ............ A61B 5/0031 |
| | | | 343/873 |
| 8,269,629 | B2 | 9/2012 | Lyon et al. |
| 8,397,971 | B2 | 3/2013 | Yates et al. |
| 8,414,577 | B2 | 4/2013 | Boudreaux et al. |
| 8,756,124 | B1 | 6/2014 | Sayers, III et al. |
| 9,000,720 | B2 | 4/2015 | Stulen et al. |
| 9,017,851 | B2 | 4/2015 | Felder et al. |
| 9,489,785 | B2 | 11/2016 | Klammer et al. |
| 9,514,341 | B2 | 12/2016 | Blair et al. |
| 9,622,808 | B2 | 4/2017 | Beller et al. |
| 9,717,565 | B2 | 8/2017 | Blair |
| 9,763,725 | B2 | 9/2017 | McPherson et al. |
| 9,826,977 | B2 | 11/2017 | Leimbach et al. |
| 10,080,813 | B2 | 9/2018 | Felder et al. |
| 10,452,875 | B2 | 10/2019 | Forster et al. |
| 11,051,806 | B2 | 7/2021 | Vendely et al. |
| 11,123,074 | B2 | 9/2021 | Adams et al. |
| 11,259,803 | B2 | 3/2022 | Shelton, IV et al. |
| 11,311,306 | B2 | 4/2022 | Shelton, IV et al. |
| 11,426,167 | B2 | 8/2022 | Shelton, IV et al. |
| 11,523,822 | B2 | 12/2022 | Shelton, IV et al. |
| 11,607,216 | B2 | 3/2023 | Krulevitch et al. |
| 11,771,419 | B2 | 10/2023 | Shelton, IV et al. |
| 11,786,240 | B2 | 10/2023 | Shelton, IV et al. |
| 2007/0272746 | A1 | 11/2007 | Ortiz et al. |
| 2009/0267765 | A1 * | 10/2009 | Greene ................ G06K 7/0008 |
| | | | 340/568.1 |
| 2011/0313894 | A1 | 12/2011 | Dye et al. |
| 2012/0111591 | A1 | 5/2012 | Shelton, IV et al. |
| 2013/0087610 | A1 * | 4/2013 | Shin ....................... G06Q 10/08 |
| | | | 235/375 |
| 2013/0247194 | A1 * | 9/2013 | Jha ...................... H04W 12/128 |
| | | | 726/23 |
| 2013/0304143 | A1 * | 11/2013 | Banville .............. A61N 1/3993 |
| | | | 607/60 |
| 2014/0276665 | A1 | 9/2014 | Lopez et al. |
| 2016/0310134 | A1 | 10/2016 | Contini et al. |
| 2017/0258401 | A1 * | 9/2017 | Volpe ................. A61N 1/37247 |
| 2018/0183874 | A1 * | 6/2018 | Cook .................... H04L 41/145 |
| 2019/0217018 | A1 * | 7/2019 | Bauss ................. A61M 5/3202 |
| 2021/0345952 | A1 | 11/2021 | Harris et al. |
| 2021/0345953 | A1 | 11/2021 | Shelton, IV et al. |
| 2021/0350895 | A1 | 11/2021 | Bakos et al. |
| 2021/0350896 | A1 | 11/2021 | Shelton, IV et al. |
| 2021/0350897 | A1 | 11/2021 | Shelton, IV et al. |
| 2022/0313145 | A1 | 10/2022 | Shelton, IV et al. |
| 2022/0313255 | A1 | 10/2022 | Shelton, IV et al. |
| 2022/0313256 | A1 | 10/2022 | Shelton, IV et al. |
| 2023/0027543 | A1 | 1/2023 | Shelton, IV et al. |
| 2023/0222454 | A1 * | 7/2023 | Cella ........................ G06N 7/01 |
| | | | 705/28 |

FOREIGN PATENT DOCUMENTS

| | | | | |
|---|---|---|---|---|
| JP | 2007145383 | A | * 6/2007 | |
| JP | 2008171446 | A | * 7/2008 | ............. A61B 90/98 |
| WO | WO-2018010931 | A1 | * 1/2018 | ............. A61B 90/90 |

OTHER PUBLICATIONS

JP 2007145383A—Container With RFID, and Package of the Container, 12 pages. (Year: 2024).*

* cited by examiner t0 = Firing begins
t1 = Delay in compensation
t2 = Firing stops
t3 = Voltage sag recovery ——— Uncompensated voltage
——— Compensation factor
- - - - Compensated voltage

SYSTEM AND METHOD FOR SELECTIVELY ADJUSTABLE DATA EXCHANGE BETWEEN A SMART PACKAGE AND A REQUESTING SYSTEM

RELATED APPLICATION

This application claims priority under 35 U.S.C. § 119(e) to U.S. Provisional Application No. 63/525,572 filed Jul. 7, 2023, the entire contents of which are hereby expressly incorporated by reference herein.

FIELD

The present disclosure relates generally to smart surgical devices, systems, and methods.

BACKGROUND

Surgical instruments are manufactured to meet specific performance metrics in order to ultimately perform a surgical procedure in a safe and effective manner. Following manufacture, surgical instruments are shipped all over the world to hospitals and surgical centers, and along the supply chain, the surgical instruments are handled by a variety of persons, including transit operators, warehouse operators, customs officials, hospital staff, surgical teams, and more.

While safe and effective performance of the surgical instrument is the goal, problems can arise. In some cases, problems with the surgical instrument may arise due to manufacturing issues. In other cases, problems may arise as a result of mishandling during transit, such as improper storage techniques or extreme environmental phenomena. In still other cases, problems may arise as a result of incompatibility with other surgical equipment or improper usage in an operating room during a surgical procedure.

Accordingly, there remains a need for improved surgical systems and methods.

SUMMARY

In one aspect, an assembly to be used for selectively adjustable data exchange with a requesting system is provided. In some embodiments, the assembly can include a medical device, and a protective container having the medical device disposed therein. The protective container can be sealed to prevent contaminates from contacting the medical device. The assembly can further include a radiofrequency identification (RFID) tag disposed within the protective container, the RFID tag including a data processor and memory storing first data and instructions. In some embodiments, the instructions can be configured to cause the data processor to perform operations including: receiving request data from a remote network in operable communication with the RFID tag, the request data characterizing a query for the first data stored in the memory to be provided to the remote network, determining, based on the received request data and a data transfer rule stored in the memory, a subset of the first data, and providing the determined subset of the first data to the remote network.

In another embodiment, the instructions can further be configured to cause the processor to perform operations comprising determining, responsive to receiving the request data, that the remote network is not authorized to receive the subset of the first data. In this embodiment, the memory can store denial data characterizing a notification indicating that the remote network is not authorized to receive the first data. In response to determining that the remote network is not authorized to receive the first data, the operations can further include providing the denial data to the remote network.

In another embodiment, the request data can include a remote network data transfer rule, and the subset of the first data can be determined based on the remote network data transfer rule.

In another embodiment, the RFID tag can further include a power source in operable communication with the data processor. The power source can be configured to store energy used to power the data processor. In this embodiment, the instructions can further be configured to cause the processor to perform operations comprising: determining whether a level of the energy stored by the power source is lower than a predetermined threshold, in response to determining that the level of the energy is lower than the predetermined threshold, generating denial data characterizing a notification indicating that the remote network is not authorized to receive the first data, and providing the denial data to the remote network.

In another embodiment, the subset of the first data can be determined based on an amount of available bandwidth of the remote network. In this embodiment, the operations can further include compressing the subset of the first data when the amount of available bandwidth of the remote network is less than a predetermined threshold.

In another embodiment, the operations can further include determining an amount of instability of the first data, and the subset of the first data can be based on the determined amount of instability. In another embodiment, the query characterized by the request data can be selectively configurable by a user via interaction with a graphical interface.

In another aspect, a system for selectively adjustable data exchange between a smart package and a requesting system is provided. In some embodiments, the system can include at least one data processor, and a memory storing first data and instructions. In some embodiments, the instructions can be configured to cause the data processor to perform operations including: receiving request data from a remote network in operable communication with the RFID tag, the request data characterizing a query for the first data stored in the memory to be provided to the remote network, determining, based on the received request data and a data transfer rule stored in the memory, a subset of the first data, and providing the determined subset of the first data to the remote network.

In another embodiment, the operations can further include determining whether the remote network is authorized to receive data characterizing the medical device and stored in the memory. In this embodiment, the subset of the first data can determined based on a result of the determining of whether the remote network is authorized to receive the determined subset of the first data.

In another embodiment, the memory can be configured to store denial data characterizing a notification indicating that the remote network is not authorized to receive the data characterizing the medical device. In response to determining that the remote network is not authorized to receive data stored in the memory, the determined subset of the first data can include the denial data.

In another embodiment, the request data can include a remote network data transfer rule, and the subset of the first data can be determined based on the remote network data transfer rule.

In another embodiment, the system of can further include a power source in operable communication with the at least one data processor, the power source can be configured to store energy used to power the data processor. In this embodiment, the operations can further include determining whether a level of the energy stored by the power source is lower than a predetermined threshold. In response to determining that the level of the energy is lower than the predetermined threshold the operations can include generating denial data characterizing a notification indicating that the remote network is not authorized to receive the data. The operations can also include providing the denial data to the remote network.

In another embodiment, the subset of the first data can be determined based on an amount of available bandwidth of the remote network. In this embodiment, the operations can further include compressing the subset of the first data when the amount of available bandwidth of the remote network is less than a predetermined threshold.

In another embodiment, the operations can further include determining an amount of instability of the first data. In this embodiment, the subset of the first data can be based on the determined amount of instability. In another embodiment, the query characterized by the request data can be configurable by a user via interaction with a graphical interface.

In another aspect, a system for selectively adjustable data exchange between a smart package and a requesting system is provided. In some embodiments, the system can include at least one data processor and a memory storing first data and instructions configured to cause the at least one data processor to perform operations including: receiving request data from a remote network in operable communication with the RFID tag, the request data characterizing a query for the first data stored in the memory to be provided to the remote network, determining, based on the received request data and a data transfer rule stored in the memory, a subset of the first data, and providing the determined subset of the first data to the remote network.

In another embodiment, the operations can further include determining whether the remote network is authorized to receive data characterizing the medical device and stored in the memory, wherein the subset of the first data is determined based on a result of the determining of whether the remote network is authorized to receive the determined subset of the first data.

In another embodiment, the memory can store denial data characterizing a notification indicating that the remote network is not authorized to receive the data characterizing the medical device, wherein, in response to determining that the remote network is not authorized to receive data stored in the memory, the determined subset of the first data includes the denial data.

In another embodiment, the request data can include a remote network data transfer rule, wherein the subset of the first data is determined based on the remote network data transfer rule. In another embodiment, the system can further include a power source in operable communication with the at least one data processor. The power source can be arranged to store energy used to power the data processor. In this embodiment, the operations can further include: determining whether a level of the energy stored by the power source is lower than a predetermined threshold. In response to determining that the level of the energy is lower than the predetermined threshold, the operations can further include generating denial data characterizing a notification indicating that the remote network is not authorized to receive the data, and providing the denial data to the remote network.

In another embodiment, the subset of the first data can be determined based on an amount of available bandwidth of the remote network. In another embodiment, the operations can further include compressing the subset of the first data when the amount of available bandwidth of the remote network is less than a predetermined threshold. In another embodiment, the operations can further include determining an amount of instability of the first data, wherein the subset of the first data is based on the determined amount of instability. In another embodiment, the query characterized by the request data can be configurable by a user via interaction with a graphical interface.

In another aspect, an assembly capable of data transference with a requesting system is provided. In some embodiments, the assembly can include a medical device, and a protective container having the medical device disposed therein. The protective container can be sealed to prevent contaminates from contacting the medical device. The assembly can further include a radiofrequency identification (RFID) tag disposed within the protective container, the RFID tag including a data processor and memory storing first data and instructions. In some embodiments, the instructions can be configured to cause the data processor to perform operations including: receiving request data from a remote network in operable communication with the RFID tag. receiving request data from a remote network in operable communication with the RFID tag, the request data characterizing a future data processing operation to be performed on a subset of the first data after the subset is transmitted from the RFID tag and a request for the subset of the first data to be transmitted from the RFID tag to the remote network, determining, based on the received request data, the subset of the first data to be provided to the remote network, and providing the determined subset of the first data to the remote network.

In another embodiment, the request data received from the remote network can include location data relating to a location of the remote network. The subset of the first data can be determined based on the location data received from the remote network.

In another embodiment, the operations can further include receiving, from the medical device, device data characterizing a history of use of the medical device and a listing of reusable components of the medical device. The operations can further include writing the received device data to the memory of the RFID tag such that the device use data is included in the first data. The operations can further include determining reusable component data characterizing the listing of the reusable components of the medical device. The operations can further include determining whether the at least one data processor is in operable communication with the remote network. In some embodiments, the determined subset of the first data can include the reusable component data when at least one data processor is determined to be in operable communication with the remote network.

In another embodiment, the operations can further include receiving, from the remote network, procedure query data characterizing a request to determine whether the medical device has been used in a surgical procedure. The operations can further include determining, based on the received device data and in response to receiving the procedure query data, whether the medical device has been used in a surgical procedure. In response to determining that the medical device has been used in a surgical procedure, the operations can further include providing the device data to the remote network.

In another embodiment, the operations can further include receiving, from the remote network, defect data characterizing a defect of the medical device. The operations can further include writing the defect data to the memory of the RFID tag such that the defect data is included in the first data.

In another embodiment, the operations can further include determining at least one component of the remote network configured to receive the determined subset of the first data and to transmit the determined subset of the first data to a recipient server. In some embodiments, the recipient server can be in operable communication with the remote network. In this embodiment, the providing can further include transmitting the determined subset of the first data to the at least one component. The providing can further include transmitting, to the at least one component, instructions configured to cause the at least one component to transmit the determined subset of the first data to the recipient server.

In another aspect, an assembly capable of data transference with a requesting system is provided. In some embodiments, the assembly can include a medical device, and a protective container having the medical device disposed therein. The protective container can be sealed to prevent contaminates from contacting the medical device. The assembly can further include a radiofrequency identification (RFID) tag disposed within the protective container, the RFID tag including a data processor and memory storing first data and instructions. In some embodiments, the instructions can be configured to cause the data processor to perform operations including: receiving request data from a remote network in operable communication with the RFID tag, the request data characterizing a location of the remote network and a request for a subset of the first data to be transmitted from the RFID tag to the remote network, determining, based on the received request data, the subset of the first data to be provided to the remote network, and providing the determined subset of the first data to the remote network.

In another embodiment, the request data received from the remote network can characterize a future data processing operation to be performed on a subset of the first data after the subset is transmitted from the RFID tag. In this embodiment, the subset of the first data can be determined based on the future data processing operation characterized by the received request data.

In another embodiment, the operations can include receiving, from the medical device, device data characterizing a history of use of the medical device and a listing of reusable components of the medical device. In this embodiment, the operations can also include writing the received device data to the memory of the RFID tag such that the device use data can be included in the first data. The operations can also include determining reusable component data characterizing the listing of the reusable components of the medical device. The operations can also include determining whether the at least one data processor is in operable communication with the remote network. The determined subset of the first data can include the reusable component data when at least one data processor is determined to be in operable communication with the remote network.

In another embodiment, the operations can include receiving, from the remote network, procedure query data characterizing a request to determine whether the medical device has been used in a surgical procedure. In this embodiment, the operations can also include determining, based on the received device data and in response to receiving the procedure query data, whether the medical device has been used in a surgical procedure. In response to determining that the medical device has been used in a surgical procedure, the operations can further include providing the device data to the remote network.

In another embodiment, the operations can include receiving, from the remote network, defect data characterizing a defect of the medical device. In this embodiment, the operations can also include writing the defect data to the memory of the RFID tag such that the defect data can be included in the first data.

In another embodiment, the operations can include determining at least one component of the remote network configured to receive the determined subset of the first data, and to transmit the determined subset of the first data to a recipient server in operable communication with the remote network. In this embodiments, the providing can include transmitting the determined subset of the first data to the at least one component. The providing can also include transmitting, to the at least one component, instructions configured to cause the at least one component to transmit the determined subset of the first data to the recipient server.

In one aspect, a system capable of data transference with a requesting system is provided. In some embodiments, the system can include at least one data processor. The system can also include a memory storing first data and instructions configured to cause the at least one data processor to perform operations. In some embodiments, the operations can include receiving request data from a remote network in operable communication with the RFID tag, the request data characterizing at least one of a location of the remote network and a future data processing operation to be performed on a subset of the first data after the subset is transmitted from the RFID tag, the request data further characterizing a request for a subset of the first data to be transmitted from the RFID tag to the remote network, determining, based on the received request data, the subset of the first data to be provided to the remote network, and providing the determined subset of the first data to the remote network.

In another embodiment, the operations can include receiving, from the medical device, device data characterizing a history of use of the medical device and a listing of reusable components of the medical device. In this embodiment, the operations can include writing the received device data to the memory of the RFID tag such that the device use data can be included in the first data. The operations can also include determining reusable component data characterizing the listing of the reusable components of the medical device. The operations can also include determining whether the at least one data processor is in operable communication with the remote network. In this embodiment, the determined subset of the first data can include the reusable component data when at least one data processor is determined to be in operable communication with the remote network.

In another embodiment, the operations can include receiving, from the remote network, procedure query data characterizing a request to determine whether the medical device has been used in a surgical procedure. The operations can also include determining, based on the received device data and in response to receiving the procedure query data, whether the medical device has been used in a surgical procedure. In response to determining that the medical device has been used in a surgical procedure, the operations can include providing the device data to the remote network.

In another embodiment, the operations can include receiving, from the remote network, defect data characterizing a defect of the medical device. In this embodiment, the operations can include writing the defect data to the memory of the RFID tag such that the defect data can be included in the first data.

In another embodiment, the operations can include determining at least one component of the remote network configured to receive the determined subset of the first data and to transmit the determined subset of the first data to a recipient server in operable communication with the remote network. In this embodiment, the providing can further include transmitting the determined subset of the first data to the at least one component. The providing can also include transmitting, to the at least one component, instructions configured to cause the at least one component to transmit the determined subset of the first data to the recipient server.

In another aspect, an assembly to be used for the exchange of executable code between a smart package and a requesting system is provided. In some embodiments, the assembly can include a medical device, and a protective container having the medical device disposed therein. The protective container can be sealed to prevent contaminates from contacting the medical device. The assembly can further include a radiofrequency identification (RFID) tag disposed within the protective container, the RFID tag including a data processor and memory storing first data and instructions. In some embodiments, the instructions can be configured to cause the data processor to perform operations including: receiving, from a remote network in operable communication with the RFID tag, request data including data characterizing a query for program data characterizing executable instructions configured to cause a remote processor to perform operations for configuring an operating system to operate the medical device, and further including data characterizing information about the remote network and/or the operating system; determining, based on the received request data, the program data characterizing executable instructions configured to cause a remote processor to perform operations for configuring an operating system to operate the medical device, and providing the program data to the remote network.

In another embodiment, the operations can further include receiving, from the remote network, second request data characterizing a query for operational data characterizing at least one control parameter for operating the medical device. The operational data can form part of the first data stored in the memory. The operations can further include determining, based on the second request data, an operational data packet that includes the operational data and operating instructions. The operational data and operating instructions can cause a remote data processor in operable communication with the remote network to operate the medical device in accordance with the at least one control parameter. The operations can further include providing the operational data to the remote network.

In another embodiment, the operations further include receiving, from the remote network, third request data characterizing a query for graphical media characterizing a graphical depiction of an operation of the medical device. The graphical media forming part of the first data stored in the memory. The operations can further include determining a graphical video based on the received third request data and the graphical media. The operations can further include providing the graphical video to a graphical display such that the at least one graphical video is displayed thereon.

In another embodiment, the determining of the graphical video is based on device usage data characterizing a frequency of use of the medical device, and the device usage data can form part of the first data stored in the memory.

In another embodiment, the device usage data is associated with a specific user of the medical device and characterizes an amount of use of the medical device by the specific user.

In another embodiment, the operations can further include: receiving, from the remote network, fourth request data characterizing a medical device parameter, determining whether a configuration attribute of the medical device matches the medical device parameter characterized by the received fourth request data, and providing data characterizing the determination to the remote network.

In another embodiment, the medical device parameter characterizes a medical device usage threshold, and the operations can further include: determining whether an amount of use of the medical device is less than the medical device usage threshold, and providing data characterizing the determination of the amount of use of the medical device relative to the medical device usage threshold to the remote network.

In another aspect, a system to be used for the exchange of executable code between a smart package and a requesting system is provided. In some embodiments, the system can include at least one data processor, and a memory storing first data and instructions to cause the at least one data processor to perform operations including: receiving, from a remote network, request data including data characterizing a query for program data characterizing executable instructions configured to cause a remote processor to perform operations for configuring an operating system to operate the medical device, and further including data characterizing information about the remote network and/or the operating system, determining, based on the received request data, the program data characterizing executable instructions configured to cause a remote processor to perform operations for configuring an operating system to operate the medical device, and providing the program data to the remote network.

In another embodiment, the operations can further include: receiving, from the remote network, second request data characterizing a query for operational data characterizing at least one control parameter for operating the medical device, the operational data forming part of the first data stored in the memory, determining, based on the second request data, an operational data packet that includes the operational data and operating instructions configured to cause a remote data processor in operable communication with the remote network to operate the medical device in accordance with the at least one control parameter, and providing the operational data to the remote network.

In another embodiment, the operations can further include: receiving, from the remote network, third request data characterizing a query for graphical media characterizing a graphical depiction of an operation of the medical device, the graphical media forming part of the first data stored in the memory, determining a graphical video based on the received third request data and the graphical media, and providing the graphical video to a graphical display such that the at least one graphical video is displayed thereon.

In another embodiment, the determining of the graphical video is based on device usage data characterizing a frequency of use of the medical device, the device usage data forming part of the first data stored in the memory.

In another embodiment, the device usage data is associated with a specific user of the medical device and characterizes an amount of use of the medical device by the specific user.

In another embodiment, the operations further include: receiving, from the remote network, fourth request data characterizing a medical device parameter, determining whether a configuration attribute of the medical device matches the medical device parameter characterized by the received fourth request data, and providing data characterizing the determination to the remote network.

In another embodiment, the medical device parameter can characterize a medical device usage threshold, and the operations can further include: determining whether an amount of use of the medical device is less than the medical device usage threshold, and providing data characterizing the determination of the amount of use of the medical device relative to the medical device usage threshold to the remote network.

In another aspect, a system to be used for the exchange of operational data characterizing at least one operation performed by a medical device between a smart package and a requesting system is provided. In some embodiments, the system can include a medical device, a protective container having the medical device disposed therein, the protective container being sealed to prevent contaminates from contacting the medical device, and a radiofrequency identification (RFID) tag disposed within the protective container, the RFID tag including a data processor and memory storing first data and instructions. The instructions can cause the data processor to perform operations including: receiving, from a remote network, first operational data characterizing at least one operation performed by a medical device, writing the first operational data to the memory, receiving, from a remote server in operable communication with the RFID tag, request data characterizing a query for the first operational data and/or the second operational data, determining, based on the received request data and the instructions, the first operational data and/or the second operational data, providing the first operational data and/or the second operational data to the remote server.

In another embodiment, the operations can further include: receiving, from the medical device, second operational data characterizing at least one operation performed by the medical device, and writing the second operational data to the memory.

In another embodiment, the remote server can be in operable communication with the remote network.

In another embodiment, the first operational data can further include data characterizing one or more surgeon reports corresponding to the at least on operation performed by the medical device, and the second operational data can further include failure data characterizing one or more operating parameters of the medical device at a time of a failure of the medical device.

BRIEF DESCRIPTION OF DRAWINGS

The present invention is described by way of reference to the accompanying figures which are as follows.

DETAILED DESCRIPTION

Figure 1:
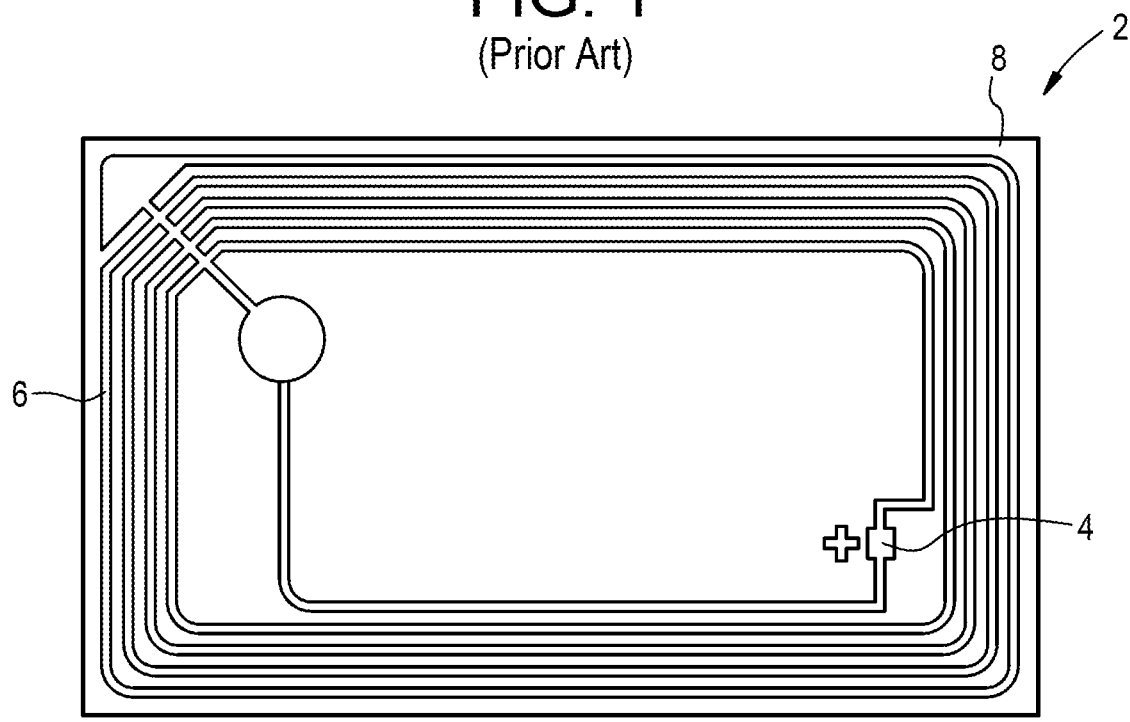
FIG. 1 is a top view of a passive RFID tag, according to an embodiment.

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the size and shape of components with which the systems and devices will be used.

Smart surgical devices, systems, and methods are provided. The use of smart devices, systems, and methods can generally enable the storing, sharing, and utilization of information throughout a supply chain. At all times, information directed to aspects of the supply chain can be logged, monitored, and reviewed in order to adjust facets of the supply chain in real time. Additionally, analysis of the compiled information can be used in order to minimize or avoid pitfalls and issues associated with the supply chain and/or products flowing through the supply chain. Overall, smart devices, systems, and methods can improve the efficiency of the supply chain through the management of information associated with products flowing through that supply chain. While the specific types of smart devices, systems, and methods can vary, in some aspects the packaging of the products themselves can be leveraged in order to consistently track, monitor, and record information associated with the products. Further, tracking devices (e.g., scanners, beacons, etc.) and/or a centralized computer management system can be employed as part of the smart systems and devices.

The use of smart surgical devices, systems, and methods can also impact the operations of a healthcare provider, such as during a surgery involving the smart surgical devices. Information can be recorded, stored, monitored, and acted upon before, during, and after a surgical procedure involving the smart surgical device in order to improve the performance and to minimize the operational risks of the smart surgical device and of future smart surgical devices.

As indicated above, in some aspects the smart devices, systems, and methods can utilize smart packaging systems, which can be included on an outer packaging containing one or more surgical instruments. In an exemplary embodiment, the outer packaging can include a power source, one or more radio frequency identification ("RFID") tags, and one or more sensors capable of measuring environmental aspects. The one or more RFID tags can take on various forms and may generally include passive and active RFID tags. Passive RFID tags can include an RFID chip (or integrated circuit, "IC"), an antenna, and a substrate. The IC contains a logical control unit, memory, and transceiver, which can be used for decoding, decrypting, and error checking. The antenna is used to receive/transmit information, such as electronic data, to and from an external electronic system with its own reception and/or transmission capabilities (e.g., a reader). The substrate holds the chip and antenna together and provides the RFID tag with structure. Passive RFID tags can receive power in the form of electromagnetic energy (e.g., radio energy) transmitted by a reader and received by the antenna of the passive RFID tag. An example of a passive RFID tag 30 can be seen in FIG. 1. The passive RFID tag 2 includes an IC 4 electronically coupled to an antenna 6. The IC 4 and the antenna 6 are mounted on a substrate 8.

Active RFID tags may include components similar to those of passive RFID tags with the addition of a separate power source (e.g., an integrated battery). Further, in some variations, other kinds of sensors or chips, such as near field communication (NFC) sensors, may be used in addition to, or in place of, the one or more RFID tags.

In some variations, the outer packaging can include additional memory storage and/or one or more additional processors in electronic communication with the one or more RFID tags in order to increase the capabilities of the RFID tags. The smart packaging system can also include one or more of a display, such as an e-ink display, LCD display, touchscreen, or equivalent, and/or a readable medium, such as a barcode, QR code, or equivalent. In some variations, the smart package system can include data ports, such as USB-type ports. With some or all of these features, the smart packaging system can generally be capable of taking in data from external sources, such as computers, computer networks, and data received from its one or more sensors, and the smart packaging system can generally be capable of transmitting data and/or presenting information to computers, computer networks, users, scanning devices, RFID readers, and any device capable of receiving data from features of the smart packaging system.

The surgical instrument(s) and/or surgical components contained within the outer packaging can vary in both form and function. In some variations, the entire surgical instrument can be a "smart" instrument in which the status and operations of the surgical instrument can be monitored, recorded, and altered at any time. For example, if the surgical instrument is an endo-cutter configured to incise and staple tissue, an amount of torque applied by the jaws of the instrument can be monitored throughout a surgical procedure. If it is determined by the HUB that too much torque is being applied by a surgeon, a maximum torque limit can be imposed wirelessly on the instrument in real time so as to prevent the occurrence of an accident. Further, with such surgical instruments, if, during an operation involving the instrument, an accident does occur, details surrounding the accident can be recorded and stored either within the memory of the package or virtually on the HUB. This information can then be used to determine the source of the accident, and, for example, whether a recall should be issued for similarly-situated surgical instruments.

In other variations, sub-portions of the surgical instrument can be "smart," while other portions of the instrument may be electronically isolated from the "smart" sub-portions such that the status and operations of the surgical instrument are not capable of being monitored, recorded, or altered whatsoever. For example, in the same endo-cutter described above, a jaw-driver sub-system may be "smart," but a sub-system concerning articulation of a shaft of the endo-cutter may not be "smart." Even though the shaft may be electronically articulable, it may not be in electronic communication with the HUB and/or the outer packaging, and it, accordingly, may be "hidden" from monitoring. These examples are exemplary only, and more concrete examples and variations are described below.

Figure 2:
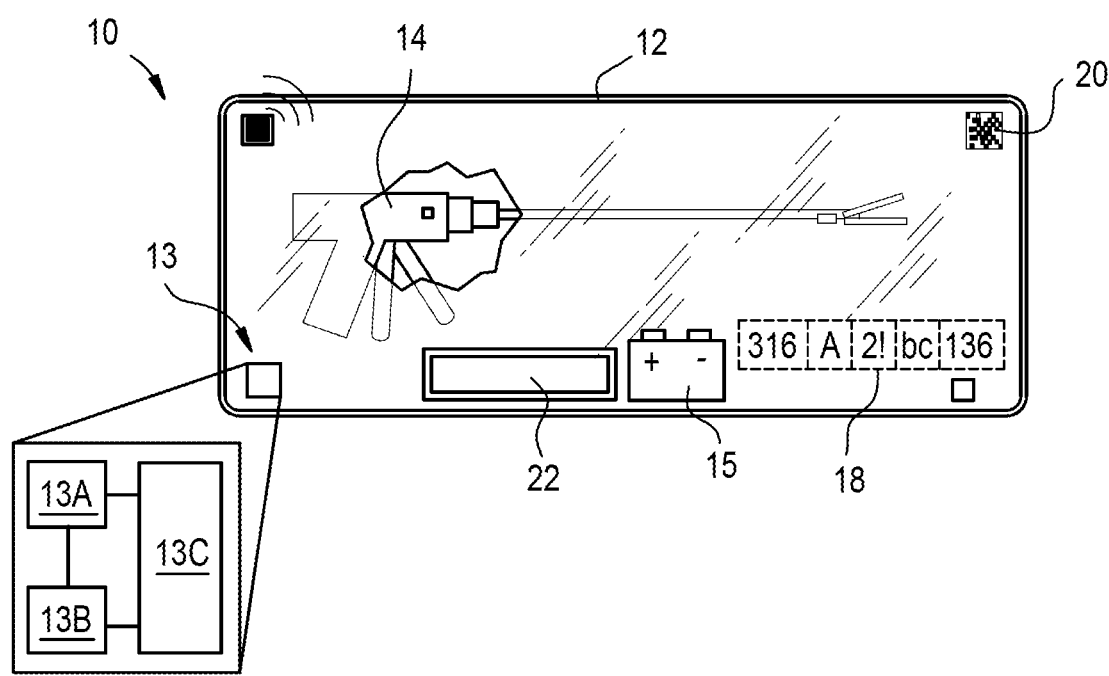
FIG. 2 is a side schematic view of a smart packaging system containing a surgical instrument according to an embodiment.

An example of a smart packaging system 10 is depicted in FIG. 2. The illustrated smart packaging system 10 includes a packaging 12 containing a surgical instrument 14 therein. The surgical instrument 14 can be any surgical instrument or surgical material, such as an endocutter as shown. The smart packaging system 10 can include a controller 13 that is configured to execute functions of the smart packaging system 10. The controller 13 can generally include a control unit 13A, a logic unit 13B, and a memory 13C that enable functionality of the controller 13. The smart packaging system 10 can also include an internal power source 15, such as a battery, that is capable of providing power to various components of the smart packaging system 10, including the controller 13, described herein. The packaging 12 can also include an RFID tag 16 configured to transmit and receive information from an external source. A serial number 18, which may or may not feature encrypted data, can be locating on the packaging 12 such that it can be read by a handler or a computer system. The packaging 12 can further include a scan-able or readable medium 20, such as a QR code or a barcode and a display 22, such as the kind mentioned previously (e.g., an e-Ink display). While not shown, the smart packaging system 10 can contain additional surgical accessories, components, and elements that may be disposed in a compartment separate from the surgical instrument 14. The surgical accessories, components, and elements can be used in conjunction with or separate from the surgical instrument 14. Together, these items can generally be referred to as the contents of the smart packaging system 10. For example, the surgical instrument 14 can be a surgical stapler, and the contents of the smart packaging system 10 can include staple cartridges that are compatible with the surgical stapler, which may be packaged within the smart packaging system 10 separate from the surgical stapler, such as in a sub-compartment of the packaging 12. Reference will be made to the smart packaging system 10 and its component parts for exemplary purposes only.

The smart packaging system 10 can receive and present information relevant to personnel who may interact with the smart packaging system 10 along the life cycle of the contained surgical instrument 14, as well as with other surgical instruments and products that interface with the contained surgical instrument 14. The kind of personnel and the relevance of the information will vary depending on where the surgical instrument 14 and the smart packaging system 10 are in their lifecycle. Following manufacture in a factory, the surgical instrument 14 will be packaged and prepared for delivery to eventually end up at a healthcare facility, such as a hospital or surgery center, to be used in a surgical procedure. To arrive at that the hospital or surgery center, the smart packaging system 10 will undergo a series of interactions with various personnel, including factory personnel, warehouse personnel, transit personnel, customs personnel, and hospital personnel. At each phase of its journey, the smart packaging system 10 can receive and transmit relevant information to personnel. Although the smart packaging system 10 can store a variety of information, the smart packaging system 10 can, based on context, selectively provide only relevant information.

Additionally, on its journey, the smart packaging system 10 may communicate with a central network, also called a HUB 50, which can monitor and coordinate information including and about the smart packaging system 10. The HUB 50 can be present along the smart packaging supply chain in the form of beacons 102 placed in key locations, such as a hospital operating room (OR). When a beacon 102 or other facet of the HUB 50 detects that the smart packaging system 10 is in close proximity, information can be exchanged between the smart packaging system 10 and the HUB 50, and information can be exchanged between the HUB 50 and various external networks.

Each beacon 102 can include a transceiver, a transponder, a power source, a processor, and a local memory. The beacons 102, generally can operate as an RFID reader in electronic communication with a central network, HUB 50. The beacons 102 can be in wired communication or in wireless communication, such as via infrared communication, radio communication, Wi-Fi communication, Bluetooth, etc. The RFID reader can be a passive reader that can receive signals transmitted by an active RFID tag, the RFID reader can be an active reader that can transmit interrogator signals and receive replies, such as authentication replies, from an RFID tag. During operation, the beacons 102 can receive transmitted data from the smart packaging system 10 characterizing information recorded by the smart packaging system 10 related it its experiences since manufacture. The beacons 102 can then transmit that received data to the HUB 50 where it can be stored, analyzed, and/or acted upon. The beacons 102 can also transmit information from the HUB 50 to a nearby smart packaging system 10.

Figure 3A:
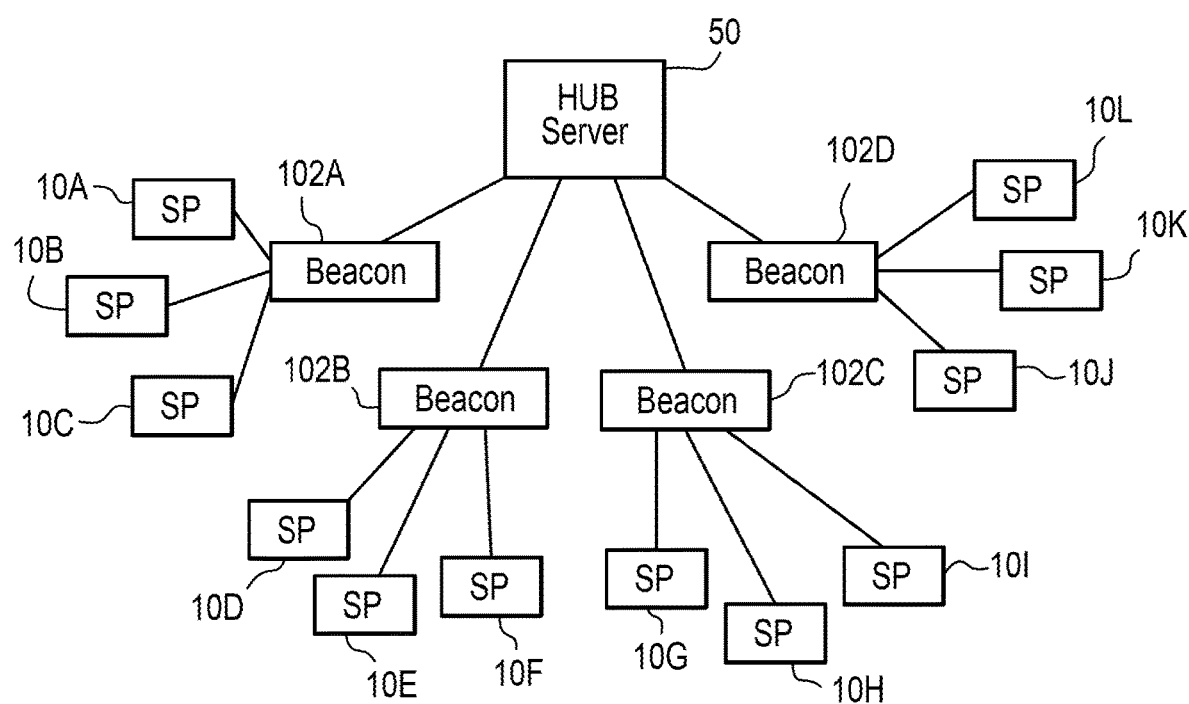
FIG. 3A is a diagram of a smart packaging system in electronic communication with at least one beacon and a HUB in an operating room, according to an embodiment.
Figure 3B:
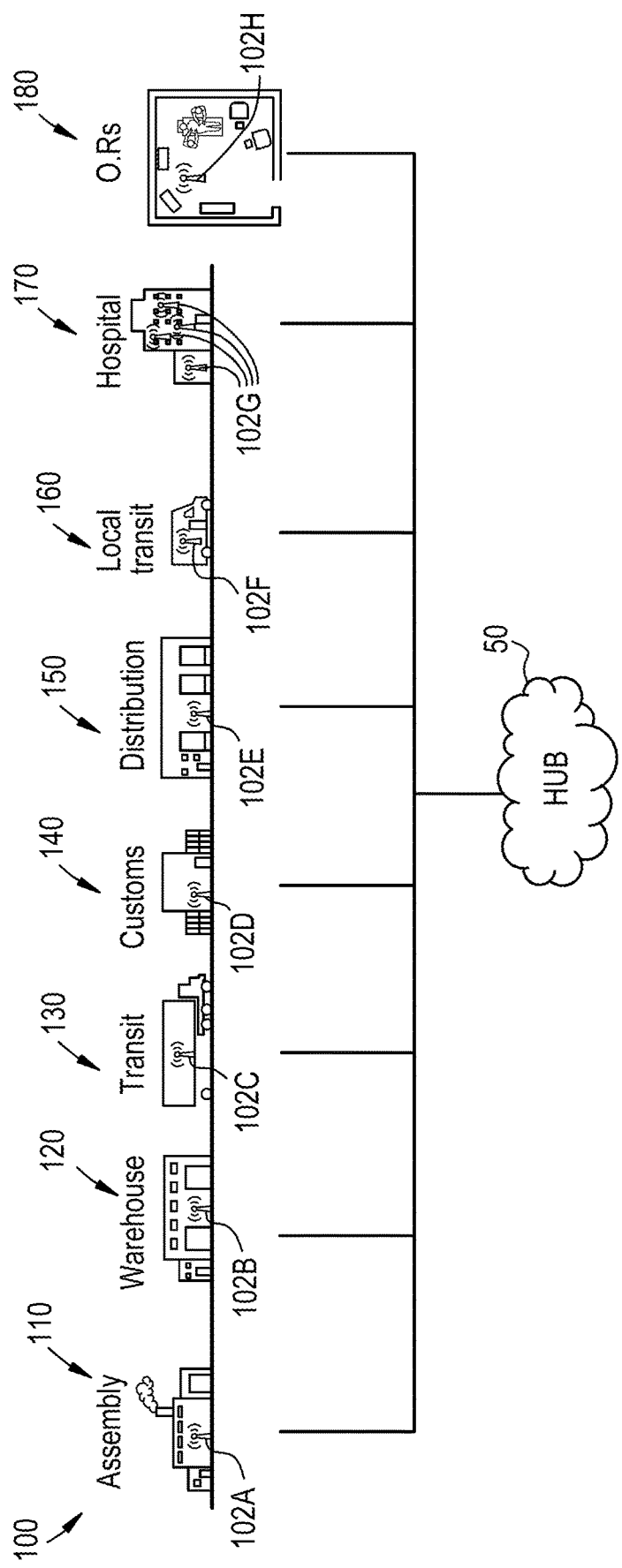
FIG. 3B is a diagram of a smart packaging system in electronic communication with a beacon and a HUB in an operating room, according to an embodiment.

A non-limiting example of the exchange of information between the beacon 102 (or HUB 50, generally) and the smart packaging system 10 is shown in FIG. 3A and FIG. 3B In FIG. 3A, a chart is depicted that shows a general hierarchy structure between the HUB 50, the beacons 102 (individually represented as beacons 102A-102D), and the smart packaging system 10 or systems 10 (individually represented as smart packaging systems 10A-10L). The HUB 50 can be in communication with the beacons 102, which can be in communication with the smart packaging systems 10. In some variations, however, the smart packaging system 10 can transmit information directly to the HUB 50 and receive information directly from the HUB 50 using its own transmission and reception capabilities. In FIG. 3B, a chart is depicted showing an exemplary supply chain 100, and different contexts in which the smart packaging system 10 may communicate with the HUB 50 via one or more beacons 102. The interplay between the smart packaging systems 10 and the HUB 50, via the beacons 102, can be important depending upon the context in which the smart packaging system 10 is located. This context can change as the smart packaging system 10 moves from manufacture to transit to use through a supply chain.

Figure 4:
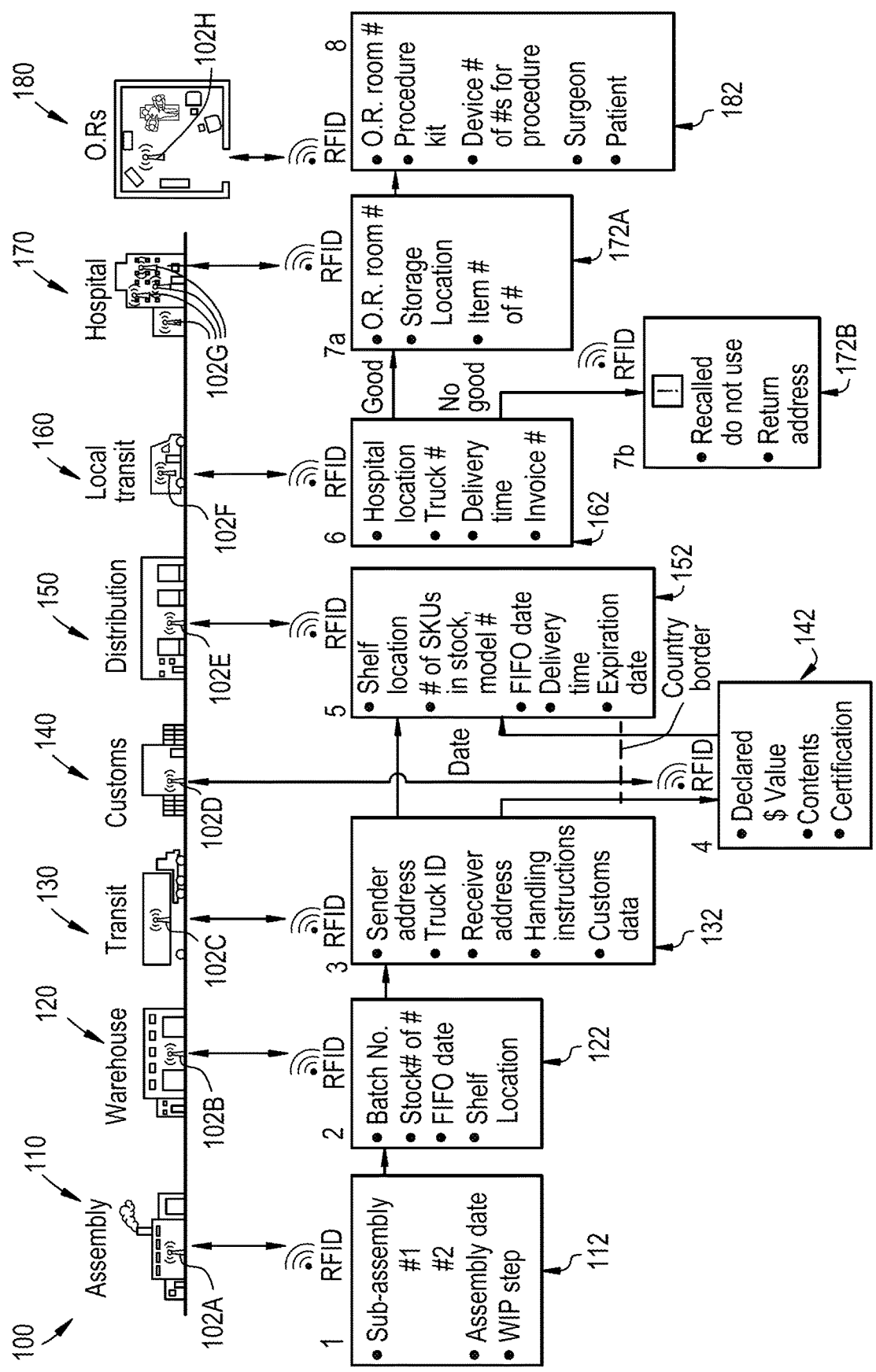
FIG. 4 is a diagram of a supply chain for a smart packaging system including a surgical instrument, and the kinds of information exchanged to and from the smart packaging system at various points along the supply chain, according to an embodiment.

The supply chain 100 shown in FIG. 3B and in FIG. 4 is shown with simplified versions of key stages along the supply chain of a surgical device or system, making the depiction of the supply chain 100 illustrative and exemplary, rather than mandatory and necessary. In reality, actual supply chains may include these stages in a different order, or they may include additional stages, duplicate certain stages, or omit stages altogether.

The first depicted stage in the supply chain 100 is the assembly stage 120, which can include a beacon 102A to facilitate communication with the HUB 50. The assembly stage 120 represents manufacture of the surgical instrument 14. Information exchanged at the assembly stage 120 can include assembly information 112 pertaining to the surgical instrument 14 itself, including its performance metrics, manufacture specifications, tolerances, safety and usage information, etc. The assembly information 112 can also include, for example, sub-assembly information pertaining to one or more sub-assemblies that are compatible with the surgical instrument. Additionally, the assembly information 112 can include work-in-progress (WIP) step and assembly date of the surgical instrument.

The second depicted stage in the supply chain 100 is the warehouse stage 110, which can include a beacon 102B. The warehouse stage 110 represents storage of the smart packaging system 10 prior to shipment thereof. Information exchanged at the warehouse stage 110 can include warehouse information 122, such as batch number, stock number and count, FIFO date, and shelf location so that the smart packaging system 10 can be tracked and located within the warehouse itself.

The third depicted stage in the supply chain 100 is the transit stage 130, which can include a beacon 102C. The transit stage 130 represents transit of the smart packaging system 10 from the warehouse to end up at a distribution center. Information exchanged at the transit stage 130 can include transit information 132, such as sender address, truck ID, receiver address, handling instructions, and customs data.

After the third depicted stage, the smart packaging system 10 may optionally be shipped across geopolitical borders, including to international locations, before ending up at a distribution center. The fourth depicted stage is the customs stage 140, which can include a beacon 102D, and it represents those occurrences when the smart packaging system 10 must cross a geopolitical border. Information exchanged at the customs stage can include customs information 142, such as declared value, contents, and certification.

If the smart packaging system 10 is not be shipped internationally, the smart packaging system can proceed from the transit stage 130 directly to the distribution stage 150. If the smart packaging system 10 is shipped internationally, it can proceed to the distribution stage 150 following the customs stage 140. The distribution stage 150 represents a warehouse or distribution center, which can include a beacon 102E that receives the smart packaging system before it is sent to its ultimate destination, such as a hospital. Information exchanged at the distribution stage 150 can include distribution information 152, such as shelf location, number of specific stock keeping units (SKUs) in stock, model number, FIFO date, delivery time, and expiration date.

The sixth depicted stage in the supply chain 100 is the local transit stage 160, which can include a beacon 102F. The local transit stage 160 represents the transit required to get the smart packaging system 10 to its ultimate destination. Information exchanged at the local transit stage 160 can include local transit information 162, such as hospital or surgery center location, truck number, delivery time, handling instructions, and invoice number. During local transit, if any aspect of the smart packaging system has been recalled, the information exchanged can include, for example, a return address, and the smart packaging system 10 can be recalled and returned for assessment and/or disposal.

The seventh depicted stage in the supply chain 100 is the hospital stage 170, which can include one or multiple beacons 102G. The hospital stage 170 represents the hospital or surgery center in which the surgical instrument 14 will be used during a surgical procedure. If local transit is able to deliver the smart packaging system 10, local transit will deliver the smart packaging system 10 to the hospital where it can be stored within the hospital until needed. Information exchanged at the hospital stage can include hospital information 172A, such as operating room (OR) number, storage location, and item count. If local transit is not able to deliver the smart packaging system 10, such as for a recall, the smart packaging system 10 can exchange recall information 172B, such as a return address for the smart packaging system, and a warning with information related to the recall.

The eighth depicted stage in the supply chain 100 is the OR stage 180, which can include a beacon 102H. The OR stage 180 represents an operating room that will use the surgical instrument 14 that is part of the smart packaging system 10. Information exchanged at the OR stage 180 can include OR information 182, such as OR room number, procedure kit details, device number in the total devices needed for the procedure, surgeon information, and patient information.

Information described at each of the stages in the supply chain 100 is exemplary only and does not represent an exhaustive list of the information that can be exchanged at a given stage.

Selectively Adjustable Data Transfer

In one embodiment, a smart package assembly is provided that is capable of providing automatic, selective data transmission via radio frequency waves using RFID technology. The smart package assembly described herein can be configured to receive request data characterizing a query for data stored in a memory of the smart package assembly. The received query data can be used by the smart package assembly to determine a portion of the data stored in the memory to be exchanged with the remote network in accordance with a data transfer rule stored in the memory.

For example, the data transfer rule can be used to determine whether the external requesting system is authorized to receive the requested data. The smart package assembly can either validate the data request and transfer the data requested, or invalidate the data request by responding to the request with data stored in the memory and characterizing a decision of denial of transmission of the requested data to the requesting system. Similarly, the smart package assembly described herein can also validate or invalidate a request based on a level of energy stored by a power source of the smart package assembly and/or based on an amount of available bandwidth of the wireless connection established between the smart package assembly and the remote network. The selectively adjustable data transfer afforded by the present disclosure can advantageously enable a medical device packaging assembly to autonomously manage the transmission of the data that it exchanges with remote networks, to maintain the security of the data stored in the smart package assembly, and to ensure that the data it provides to remote networks can consistently be transferred accurately.

Figure 5:
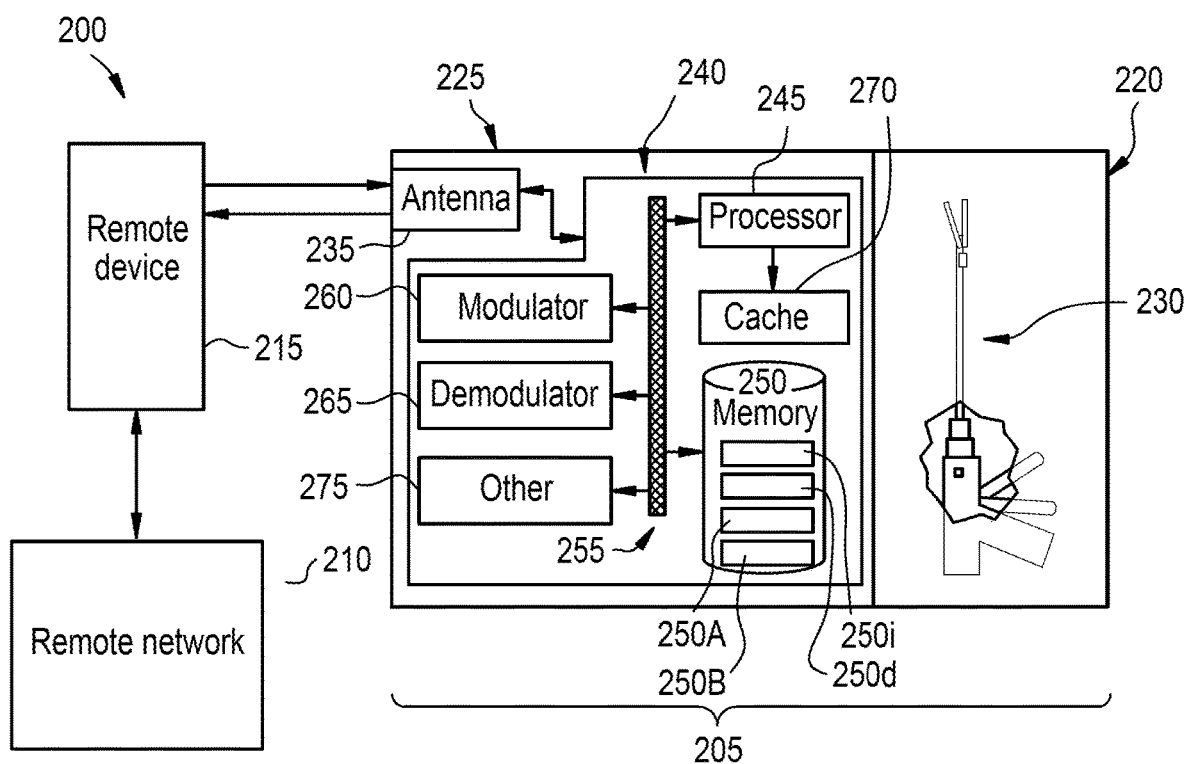
FIG. 5 is a diagram illustrating a radio frequency communication system including a medical device, a protective container having the medical device disposed therein, and an RFID tag disposed within the protective container.

FIG. 5 is a diagram illustrating a communication system 200 including a smart package assembly 205 and a remote network 210 communicatively coupled to at least one remote device 215. In some embodiments, the remote device 215 can include, but is not limited to, an RFID reader, an RFID beacon, or any other device that is configured to exchange data with the RFID tag as described herein, and can form one of the components of the "HUB" described above. The remote network 210 can be configured to exchange data with all of the remote device 215 as described in further detail below.

In some embodiments, the system 200 can include a plurality of remote devices 215 which form part of a remote device network installed at multiple places at a given location within the supply chain described above, which is may comprise one or more of the components of the "HUB" described elsewhere herein, and the one or more remote devices 215 can be communicatively coupled to the remote network 210.

In some embodiments, the remote network 210 can include a remote server system that is located at a facility that is different from that at which the remote device 215 is installed. In some embodiments, the remote device 215 can be configured to communicate with the remote network 210 over an external network (e.g., the internet). In other embodiments, the remote network 210 can include a site local server system located at the facility at which the remote device 215 is installed. In some embodiments, the remote device 215 can also be configured to communicate with the remote network 210 via a hard wired connection or via a wireless communication protocol.

As explained above, the smart package assembly 205 can include a protective container 220 and a radiofrequency identification (RFID) tag 225 disposed on or within the protective container 220. The protective container 220 can have a medical device 230 or other component disposed therein, and the protective container 220 can be sealed to prevent contaminates from contacting the medical device. In some embodiments, the RFID tag 225 can have a similar architecture as that of RFID tag 2 of FIG. 1, including an antenna 235 electronically coupled to an integrated circuit (IC) 240, both of which are mounted on a substrate (not shown).

In some embodiments, the RFID tag 225 can include a degradable/modifiable element that is designed to degrade over time. This can prevent old tags from being reused in counterfeit applications. For example, in some embodiments, the RFID tag 225 can be made using a plurality of strands of different polymers, each of which having a different degradation property (e.g., Some of the polymers can be gamma sensitive, others humidity sensitive, others temperature sensitive, others light sensitive, etc. When the circuit is closed, it enables the RFID tag 225 to function. However, when one or more of the strands is exposed to the environmental factors it is sensitive to, it can be configured to break down, causing the circuit to be opened and disabling the RFID 225.

In some embodiments, the integrated circuit 240 can include at least one processor 245 and a memory 250 in operable communication with the processor 245. The memory 250 can store data characterizing instructions 250$i$ that, when provided to the processor 245, cause the processor 245 to execute one or more processes in accordance with the instructions 250$i$. The memory 250 can also store a plurality of subsets of data 250A, 250B that can characterize one or more attributes of the medical device 230, the RFID tag 225 (including components thereof), and/or the protective container 220, as well as other aspects of the smart package assembly 205 and its constituent components described elsewhere in detail herein. Although the memory 250 is described herein as storing a plurality of subsets of data, in some embodiments the memory 250 can store a single set of data characterizing one or more of these attributes and/or aspects. Similarly, although the memory 250 is described as storing subsets of data 250A, 250B, in some embodiments the memory 250 can store additional subsets of data beyond the subsets of data 250A, 250B described herein. The memory 250 can be any device suitable for storing computer readable data. The memory can be a device with fixed storage or a device for reading removable storage media. Examples include all forms of non-volatile memory, media and memory devices, semiconductor memory devices (e.g., EPROM, EEPROM, SDRAM, flash memory devices, and all types of solid state memory), magnetic disks, and magneto optical disks. The integrated circuit can have any number of memory devices.

As illustrated in FIG. 5, the processor 245 is in communication, via a connection bus 255, with a modulator 260, a demodulator 265, and the memory 250. The processor 245 incorporates, or is directly connected to, a cache memory 270. The cache memory 270 is generally a form of high-speed computer memory placed in close proximity to the processor for fast read/write times. In some implementations, the cache memory 270 is part of, or on the same chip as, the processor 245. Processes that can be performed by the processor 245 can include, but are not limited to, determinations of exact subsets of data of the subsets of data 250A, 250B stored on the memory 250 to transfer to the remote device 215 via the antenna 235 as described in additional detail below. The processor 245 can be any logic circuitry that processes instructions, e.g., instructions fetched from the memory 250 or cache 270. In many embodiments, the processor 245 is an embedded processor, a microprocessor unit or special purpose processor. The integrated circuit 240 can be based on any processor, e.g., suitable digital signal processor (DSP), or set of processors, capable of operating as described herein. In some embodiments, the processor 245 can be a single core or multi-core processor. In some embodiments, the processor 245 can be composed of multiple processors.

The modulator 260 can be configured to convert digital data that is stored on the RFID tag into a radio frequency (RF) signal that can be transmitted by the antenna 235. In some embodiments, the modulator 260 can modulate the digital data stored it onto an RF carrier signal using a modulation technique such as amplitude modulation (AM), frequency modulation (FM), phase modulation (PM), or any other modulation technique known in the art. Alternatively, the demodulator 265 can be configured to convert the RF signal that is received by the antenna 235 into digital data. In some embodiments, the demodulator 265 can be configured to demodulate the received RF signal to extract the digital data by stripping the data from the RF carrier signal, using techniques such as amplitude demodulation, frequency demodulation, or phase demodulation, or any other known demodulation technique known in the art. In some embodiments, the modulator 260 and demodulator 265 can be integrated in the same circuit to form a singular modulation/demodulation modem.

In some embodiments, the IC 240 can further include other devices 275. Examples of other devices 275 include, but are not limited to: a power supply configured to store and supply power to the RFID tag, a power management component configured to manage power consumption of the RFID tag, encryption/decryption hardware configured to encrypt/decrypt data generated by and/or stored by the RFID tag to enhance the security of the RFID tag, a GPS device configured to determine location data characterizing the location of the tag, and/or sensors (e.g. a temperature sensor, an accelerometer, a magnetic sensor, a light sensor, etc.) to monitor the environment of the RFID tag and to generate data characterizing the environment in which the RFID tag is located. As explained above, the memory 250 can be configured to store data including, but not limited to, instructions 250$i$ configured to cause the data processor 245 to perform one or more operations. And, as explained above, the memory 250 can also store data including plurality of subsets of data 250A, 250B pertaining to the smart package assembly 205 and/or the medical device 230 disposed therein. For example, the instructions 250$i$ stored in the memory can include rules for transmission of data stored in the memory 250. In some embodiments, the instructions 250$i$ can characterize data transfer rules defined based on the plurality of subsets of data, a level of power in a power source of the assembly, and data in the request data, which can include, for example, a query for a specific subset of the plurality of subsets of data, a location of the requesting remote device, an intended use of the requested data, etc. The plurality of subsets of data 250A, 250B can include, but are not limited to, a location of the assembly 205, a type of medical device 230 stored in the assembly 205, a historical log of the assembly 205 (e.g. previous locations or damage), and other forms of data characterizing the medical device. The data regarding the medical device 230 can include, for example, a historical log of usage statistics, previous failures, previous maintenance and/or replacements, previous interactions with other devices, etc. The data regarding the medical device 230 can also include a list of components of the device, an intended use for the device, and instructions on how to use the device.

In some embodiments, the plurality of subsets of data 250A, 250B can further include denial data 250$d$ including notifications indicating a refusal to transmit the requested data based on a rule in the instructions 250*i*. The denial data 250*d* can be transmitted to the remote device in the response data in the event where it is determined by the processor, that the remote device is unauthorized to receive the requested data. The denial data 250*d* can also be transmitted in the response data in the event that the assembly 205 does not have the data requested. The denial data 250*d* can also be transmitted in the event that a power source of the assembly 205 is too low to communicate with requesting devices.

As explained above, in some embodiments, the RFID tag 225 can be configured to receive request data from a remote device 215 in operable communication with the RFID tag 225. In some embodiments, the request data can include data characterizing a query for a subset of the data stored in the memory to be provided to the remote device (e.g., 250A or 250B). In some embodiments, the request data can include data characterizing an intended use of the subset of data 250A (or 250B) by the remote device 215 and/or the remote network 210. An example of such data can include data characterizing an attribute that indicates that the subset of data 250A or 250B will be utilized in downstream computing operations required in response to issuance of a company Product Inquiry (PI). A PI issuance can be made, for example, in the event that multiple client reports received by a company have led to the company to decide that a specific product or component may need to be recalled. In the event of a PI, rather than pulling data from all of the packages and sending the company an excessive amount of data that has to be filtered upon receipt, the system described herein allows for an automated and targeted acquisition of data based on what information is desired. Accordingly, in some embodiments, the RFID tag 225 can be configured to determine response data based on the received request data and a data transfer rule of the instructions 250*i* stored in the memory 250.

In some embodiments, the smart package assembly 205 can further include one or more separate return packages (not shown) for returning all or separate parts of the medical device 230 to various return locations as described in further detail below. In some embodiments, the return packages can be similar to the smart package assembly 205 and can be configured to operate similarly to the smart package assemblies described herein. In some embodiments, the return package could also be a non-smart package (e.g. a box and/or other simple container lacking the RFID functionality described herein). In some embodiments, the smart package assembly 205 can be configured to transfer operational data to the return package and appended the data to the data stored in the return package to be analyzed by a recipient of the return package.

In some embodiments, when the smart package assembly 205 is a return package, the flow of data can be reversed, and the remote device can be configured to transmit data (e.g. operational data) to the assembly 205. In this embodiment, the data transmitted to the assembly 405 can be appended to the data stored thereon to be analyzed upon return by the recipient of the return package (e.g. the manufacturer), as will be discussed in greater detail below.

In some embodiments, the request data can further include location data characterizing a location of the remote device 215, and, the response data can be determined based on the location data transmitted by the remote device 215. In some embodiments, the location data can originate from the remote network 210 from which the request data is received by the remote device characterized by the location data. In some embodiments, the location data can originate from the remote device 215 that is characterized by the location data. Location data can be an important aspect of the request data, as the data that is useful to any single point in the supply chain can differ greatly, and furthermore, data transfer protocols can vary depending on location. For example, in the event that a PI results in a product recall or product disposal, location data can be imperative, as return/reusability protocols can vary depending on the location of the smart package assembly 205 at any given point in the supply chain. For example, certain devices may not be able to be shipped via plane or other mode of transport depending on the location of the smart package assembly 205 at any given point in the supply chain. As another example, in the European Union, batteries in some devices may be required to be disposed of separately from the device, while in the United States, that may not be the case. Accordingly, in such an exemplary use of the functionality described above, a smart package assembly 205 could be sent to a country with data characterizing all possible return addresses for the smart package assembly 205 stored in the data thereon. Upon receipt of the smart package assembly 205 at a location at which the remote device 215 is installed, the return package could then be configured to receive the location data from the remote device 215 in the vicinity of the smart package assembly 205. Based on the location data included in the request data, the smart package assembly 205 could be configured to choose a return address from the possible return addresses in the event of a recall, based on a preprogrammed set of return rules.

In some embodiments, the medical device 230 can include an RFID tag (not shown) having one or more of the components and/or aspects of functionality described herein with respect to the RFID tag 225. Such an RFID tag can, in some embodiments, be in operable communication with the RFID tag 225 as well as the remote device 215, independent of the RFID tag 225, as described in further detail below.

Figure 6:
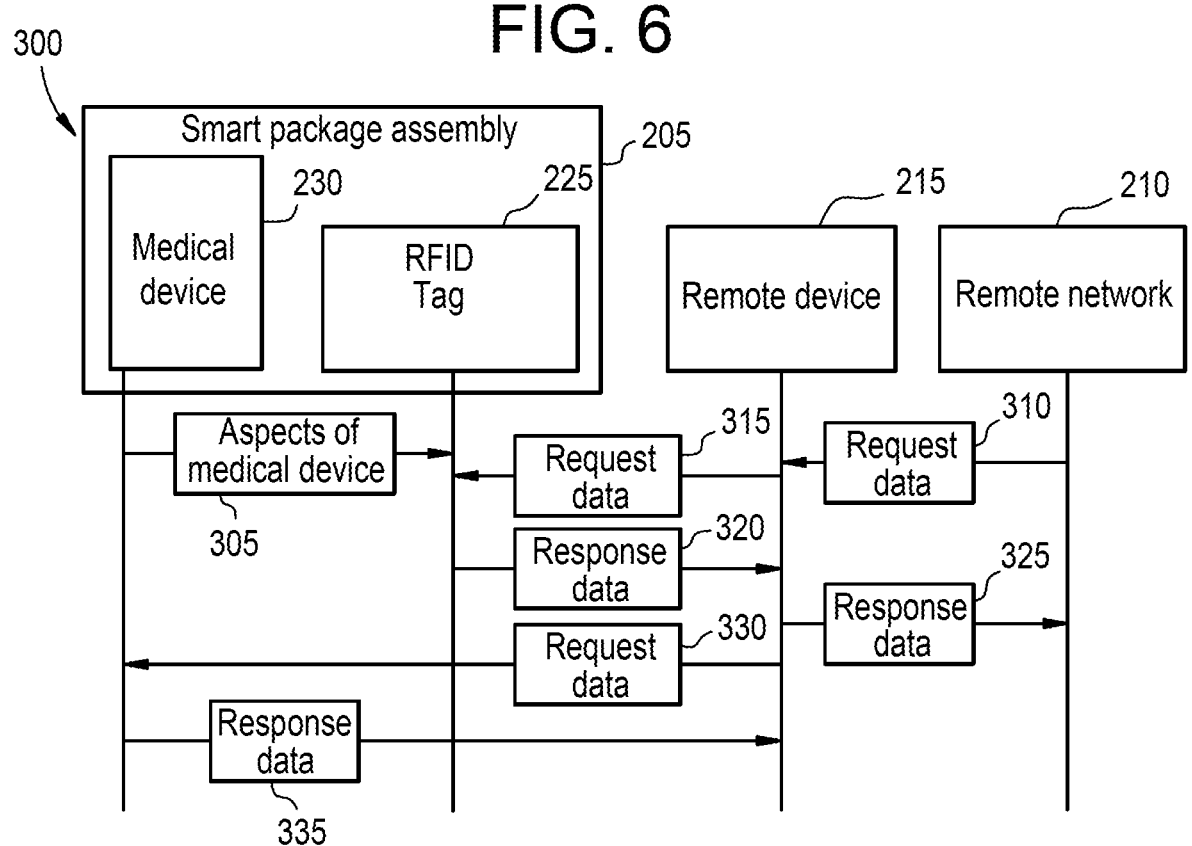
FIG. 6 is a flow diagram illustrating an exemplary process for selectively adjustable data transfer between components of the system of FIG. 5.

FIG. 6 is a diagram 300 illustrating an exemplary process for selectively adjustable data transfer between components of the smart package assembly 205 (e.g., the RFID tag 225 and/or the medical device 230), the remote device 215, and the remote network 210.

In some embodiments, the RFID tag 225 can, at 305, receive data characterizing one or more aspects of the medical device 230. For example, in some embodiments, the received data can include data characterizing a history of use of the medical device 230 as well as a listing of reusable (harvestable) components of the medical device 230. In some embodiments, the historical use data can include, for example, a past locations log, a past surgical operation log, a past failures log, a past maintenance log, etc. In some embodiments, the received data can comprise a part of the plurality of subsets of data 250A, 250B.

In some embodiments, the remote network 210 can, at 310, transmit request data to the remote device 215, and the remote device 215 can, at 315, transmit the request data to the smart package assembly 205. In some embodiments, the request data can include data characterizing a query for the data stored in the memory 250 of the RFID tag 225. In some embodiments, the remote network 210 can transmit data characterizing an instruction to the remote device 215 to cause the remote device 215 to transmit the request data.

In response to receiving the request data, the processor 245 of the RFID tag 225 can use the request data and/or instructions stored on the memory 250 (e.g., one or more data transfer rules) of the RFID tag 225 to determine response data that it will transmit to the remote device 215, and, at 320, the response data can be transmitted from the RFID tag 225 to the remote device 215. The remote device 215 can, at 325, transmit the response data to the remote network 210 for further processing by other electronic components in operable communication with the remote network 210.

In some embodiments, as discussed above, the data stored on the package 205 and/or the device 230 can be encrypted using public-key encryption. Accordingly, in some embodiments, the response data can be encrypted using a public key, and transmitted to the remote device 215. In this case, the remote device can be configured to request a corresponding private key from the remote network 210. Once the remote device 215 has received the private key from the remote network, the remote device 215 can use the private key to decrypt the public-key encrypted response data.

In some embodiments, the data stored on the package 205 and/or the device 230 can be encrypted using symmetric encryption. In some embodiments, for example, in a system that requires more security, the system can be configured to use threshold cryptography. In this case, the package 205 and the medical device 230 can both be configured to have separate keys that need to be combined in order to unlock the package 205 and/or the medical device 230 for use. In threshold cryptography, the package 205 and the medical device 230 can be assigned a private key and a corresponding public key. In this case, he public keys can be combined to form a composite public key, which can be used to encrypt the response data. Similarly to as described above, the remote device 215 can be configured to request the corresponding private keys from the remote network 210. Once the remote device 215 has received the private keys from the remote network, the remote device 215 can use the private keys together to decrypt the encrypted response data.

As referenced above, the response data can be determined based on the received request data and/or in accordance with one or more data transfer rules. For example, the determined response data can differ based on whether the request data is validated in accordance with the data transfer rules. More specifically, if the request is validated, the assembly 205 can determine response data that is responsive to the query characterized by the request data. Alternatively, if the request is not validated, the assembly 205 can transmit response data that includes denial data characterizing a notification that the query characterized by the request data has been refused in accordance with one or more of the data transfer rules stored on the memory 250. Alternatively, in some embodiments, upon determining that the query characterized by the request data is not validated, the assembly can be configured to simply not respond to the request. The use of selectively adjustable data transfer, as illustrated by this example, can be advantageous in any application that requires validation of a query characterized by the request described above, authentication of the query, and/or error checking of the data being sent in response to the query characterized by the request data received by the smart package assembly 205.

In some embodiments, the processor of the RFID tag 225 can be configured to determine the subset of data that it will transfer based on other instructions stored on the memory. For example, in some embodiments, the request data can include data characterizing the remote device 215 location, intended use of the requested data, medical device 230 requirements, or other information. The assembly 205 can be configured to receive the request, and compare the request data to data stored thereon characterizing the smart package assembly's 205 actual and/or future location, the medical device's 230 intended use, medical device 230 specifications, and/or power level of the smart package assembly 205 (if powered by a power supply), and the like. The processor can be configured to determine the subset of the data to be transmitted, and respond to the request based on the results of said comparing.

For example, in the event that the assembly 205 is equipped with a power source, responsive to any request, the assembly 205 could be programmed to check the current power level of the power source before providing any data. Accordingly, based on the decisions made by the assembly 205, the response data provided can include the data which is responsive to the query characterized by the request data that is received from the remote device 215, however, in the event that the request is denied or limited, the response data provided can be different from that which is responsive to the query. For example, in the event that the assembly 205 determines that the remote device 215 is not authorized to receive the subset data requested, the assembly 205 can retrieve the denial data from the memory and transmit the denial data as response data to the remote device 215 indicating that the remote network 205 is not authorized to receive the subset of data requested. In the example described above, the assembly 205 could refuse a request for information in the event that low power is determined in order to save on power, regardless of the type of data request received. In some embodiments, the processor could be programmed with logic resembling IF-THEN logic. For example, logic programmed on the processor 245 could resemble something similar to, but not limited to: IF (power<comm_threshold) {transmit_data(denial_data);} else {transmit_data(requested_data);}. This logic establishes that responsive to a request from a remote device 215, if a power level of a power source of the assembly 205 ("power") is less than a predetermined communication power level threshold ("comm_threshold"), then the assembly 205 can be configured to retrieve the denial data from the memory 250 and transmit it to the remote device 215 as response data ("transmit_data(denial_data)"). Alternatively ("else"), this logic establishes that if the power level of the power source of the assembly 205 ("power") is not less than a predetermined communication power level threshold ("comm_threshold"), then the assembly 205 can to retrieve data corresponding to request from the memory and transmit it to the remote device 215 as response data ("transmit_data (requested_data)").

A person skilled in the art will appreciate that the features described above can be used in a communication system having a variety of other configurations, and that the example provided above is merely one exemplary embodiment. Other embodiments of communication systems are disclosed in U.S. Patent Publication No. 2023/0027543, titled "Monitoring Power Utilization and Needs within Surgical Systems" filed on Jul. 23, 2021, which is hereby incorporated by reference in its entirety.

In another example, RFID tag 225 of the assembly 205 can be programmed with a list of access codes that correspond to specific types of data stored thereon, and the request data sent from the remote device 215 can include data characterizing a specific access code. In some embodiments, the assembly 205 can be configured to only provide the data responsive to the query characterized by the request data as response data if the access code in the request data matches an access code stored on the memory. In another example, the data stored on the memory can be encrypted or otherwise encoded in a secure manner. In this embodiment, the response data can only be read by the remote device 215 if the request data includes the correct decryption key. This can help to protect the data from unauthorized access.

In another example, the data stored on the memory can include data characterizing a destination location and/or checkpoint locations (e.g. locations 110-180 depicted in FIG. 4) along with current location data characterizing a current location of the assembly 205 and/or the medical device 230. In this embodiment, the request data can include data characterizing the remote device 215 location, and the assembly 205 can be configured to only transmit data to remote devices 215 that are within a certain range of the current location of the assembly 205 and/or medical device 230 and/or to remote devices 215 that are within a certain range of the destination location and/or checkpoint location stored on the memory 250 and/or medical device 230. This can be useful for controlling access to specific data or for limiting the amount of data that is transmitted at any given time.

In some embodiments, the request data transmitted from the remote device 215 can include a remote device and/or remote network transfer rule. The remote device 215 and/or the remote network 210 can include such a rule in the request data, and the assembly 205 can be configured to transmit response data based on the remote device and/or remote network transfer rule included in the request data. Such a transfer rule(s) could include, for example, a simple command similar to "Read Subset 1". This command could be received by an antenna 235 of the RFID tag 225 of the smart package assembly 205 (as part of the request data) and then passed to the processor 245 (and/or microcontroller) of the RFID tag 225. Responsive to this command, the assembly 205 could be configured to retrieve the subset 1 data stored on the memory and transmit it back to the remote device 215 as response data.

In some embodiments, data transfer rule(s) stored on the memory 250 could include a search operation to be performed on the data stored on the memory 250. In this embodiment, the processor can be configured to search through the data stored on the memory for a specific string, or other form of information. In some embodiments, the data transfer rule(s) could include logic. For example, the transfer rule could include logic such as "Read Subset 1 if intended use is endoscopic heart surgery." In this embodiment, the processor 245 can first check data characterizing the intended use of the medical device 230 before deciding whether the response data should include data corresponding to the received request data, or data characterizing the denial data. Again, in this embodiment, the assembly could also be configured to simply not respond to the request data, rather than responding with data characterizing denial data. In some embodiments, the transfer rule(s) can be used in combination with rules inherent to the assembly 205 (e.g. the energy level threshold check discussed previously).

In some embodiments, the data storage capabilities of the RFID 225 and/or of the medical device 230 stored in the assembly 205 can be limited. Accordingly, it can be advantageous for the RFID 225 to either redact unimportant data and/or compress data in order to increase storage capability and/or lessen the amount of data to be transferred to/from the RFID tag 225. Additionally, the remote device 215 can have a limited bandwidth—in which case compressed and/or refined data transmission can be desirable. Accordingly, the RFID 225 can be configured to only record data that is "important". "Important" data can include anomaly event data including, but not limited to, medical device 230 errors/failures, location checkpoints, assembly 205 damage, etc. In this case, all other data can be determined to be "unimportant" and can be marked as redacted to limit the amount of data stored on the memory 250. Unimportant data can include, for example, data characterizing operational data of the medical device 230 stored on the memory 250 of the RFID tag 225 and/or on the medical device 230 that is within an operational range.

The RFID 225 can also be configured to utilize data compression processes to allow for greater storage capability and to allow for more efficient data transmission to the remote device 215 in the event that the remote device 215 has limited bandwidth. Data compression can be achieved by simply deleting or truncating the data, replacing stings of data with simple characters to identify that something was redacted, or by using several data compression algorithms. Examples of data compression algorithms that can be used can include, but not be limited to: Lempel-Ziv-Welch (LZW) or Lempel-Ziv 77 (LZ77) compression, Huffman coding compression Run-length encoding compression, Arithmetic coding compression, and/or Deflate data compression. Accordingly, in some embodiments, the response data transmitted can be determined based on an amount of available bandwidth of the remote device 215. In some embodiments, the response data transmitted can also be compressed responsive to determining, by the remote device 215, that the amount of available bandwidth of the remote device 215 is less than a predetermined threshold.

In some cases, there can be a loss of data stored on the memory, or there can be instability in the data stored. In some cases the data stored on the memory can be inaccurate or missing, which can cause errors in the information that is read by the remote device 215. Further, the RFID tag 225 may lose data due to interference from other systems which can lead to the data stored becoming corrupted or unreadable. In other cases, the data stored can change in an unexpected way due to environmental conditions or power levels, or some other factor, which can cause errors in the data. In other cases, the memory can be limited, and an overflow of data transmitted from the medical device 230 and/or various remote devices 215 of the remote network can result in data loss if not handled properly. Alternatively, the data can simply deteriorate over time, becoming unreadable or inaccessible.

In some embodiments, it can be desirable for either the remote device 215 and/or the assembly 205 to be able to determine an amount of data instability when determining the request data and/or the response data respectively. Accordingly, in some embodiments, the assembly 205 can be configured to prioritize newer data over older data and/or more important data over unimportant data when determining the response data. By prioritizing transmitting newer data and/or more important data first, the assembly 205 can be more resistant to losing new/important data in the event of a power loss or data interference. In some embodiments, the prioritization instructions can be included in the instructions stored in the memory. In other embodiments, the prioritization instructions can be included in the transfer rule(s) transmitted by the remote device 215 of the remote network 210. The assembly 205 can also be configured to prioritize data based on anomaly events, or errors or failures. For example, if the medical device 230 stored in the assembly 205 is a surgical stapler, and battery power starts to decline or if catastrophic power loss occurs, the processor of the assembly 205 and/or the stapler 230 can be configured to repeat its last known data stream as response data. Additionally, in a similar crisis event, the remote device 215 can be configured to enter a quick data harvest mode to increase the frequency or sampling rate that it requests data from the assembly 205.

In some embodiments, the amount of data instability can be determined by regularly performing data integrity checks to ensure that the data stored on the memory is complete and accurate. In some embodiments, the amount of data instability can be determined using parity checks. Parity checks can detect errors in data by adding an extra bit, called a parity bit, to the data. In some cases, the parity bit can be set to 0 or 1, and when the response data is transmitted to the remote device 215 the parity bit can be used to check if the data is correct. Integrity checks can also be performed using Cyclic Redundancy Checks (CRC) or any other hash function that is configured to aid in integrity checking. CRCs work by taking a block of data, such as the response data to be transmitted to the remote device 215, and perform a mathematical calculation on it to produce a fixed-size output that can be a first CRC value. When the response data is received by the remote device 215, the same calculation can be performed to output a second CRC value that can be compared to the first CRC value. In some cases, CRCs (or other hash functions) can be better suited for integrity checks than parity checks, as they can detect errors in any bit of the data, not just a single bit. CRCs also provide more information about where the error occurred in the data than do parity checks, however either method can be used. Other methods that can be used to determine the amount of data instability can include checksums, hash functions, and other digital signature methods.

While parity checks, CRCs, checksums, hash functions, and other error detection methods can be useful in determining the integrity of data, they are not capable of correcting errors. Accordingly, in some embodiments, integrity checks performed using error-correcting codes (ECC) or other methods. ECCs are algorithms that can be used to detect and correct errors in the data that is stored on the memory by adding redundant data to the original data, allowing for errors to be detected and corrected without the need for retransmission. Other methods that can be used to detect and correct errors in data being transmitted can include Forward Error Correction (FEC) codes, Reed-Solomon codes, and Hamming codes.

In some embodiments, the query characterized by the request data can be selectively configurable by a user via interaction with a graphical interface (GUI). In some embodiments, the GUI can be integral with the remote device 215 and/or the assembly 205 (e.g. display 22 as illustrated in FIG. 2).

In some embodiments, the remote device 215 can be configured to communicate with the medical device 230 directly in a manner that is similar to the communication functionality described above between the remote device 215 and the smart package assembly 205. In this case, the remote device 215 can send, at 330, request data to the medical device 230, and the medical device 230 can be configured to determine response data and transmit data at 335 back to the remote device 215.

The current subject matter provides many technical advantages. For example, as explained above, some embodiments of the RFID tags provided on the smart package assemblies described in the current subject matter can receive a request for data from a remote device and selectively adjust data stored in a memory of the RFID tag to transmit to the requesting device in accordance with the request and a set of data transfer rules. This can advantageously allow the RFID tags described herein to permit the transfer of only that data which is responsive to the request received from the remote device and prohibit the transfer of additional data which is not relevant or responsive to the received request. Notably, as a result of the selectively adjustable data transfer enabled by the current subject matter, as described above, a reduced amount of data can be transferred from the RFID tags and the requesting remote devices, which can permit the transmission of data responsive to the received request that would not otherwise be possible due to restrictions in the bandwidth of the RF communications used to transfer data between the RFID tags and the requesting remote devices. Additionally, as the current subject matter results in a reduced amount of data transferred from the RFID tags, analysis and processing of the data responsive to the request can be performed faster and/or with fewer computational resources than would otherwise be required.

Other technical advantages can include improved security of data stored in smart package assemblies, as well as better power management of powered smart package assemblies. As explained above, the selectively adjustable data transfer described herein allows for the validating and invalidating of data requests based on a number of data transfer rules and permissions. Such selectively adjustable data transfer can help prevent unauthorized access to sensitive information characterized by the data stored in the memory of the RFID tags, which existing systems may be unable to provide. Further, as the current subject matter results in a reduced amount of data transferred from the RFID tags in an embodiment in which that the smart package assembly is powered by a power source, the selectively adjustable data transfer functionality described herein can help to reduce the power required from a power source to transmit the data responsive to the request. Similarly, some embodiments of the functionality described herein can eliminate the transmission of erroneous and/or incomplete data by denying requests for data if an energy level of the power source is below a certain threshold.

Packaging Awareness

In another embodiment, a smart package assembly is provided that is capable of providing automatic, selective data transmission via radio frequency waves using RFID technology. The smart package assembly described herein can further determine the data that it will exchange with external requesting system based on an intended use of the data by the requesting system and/or a location of the requesting system. The smart package assembly described herein can advantageously be aware of its location, and make decisions about the data that it exchanges with external requesting systems based on its own location relative to requesting systems' locations.

Figure 7:
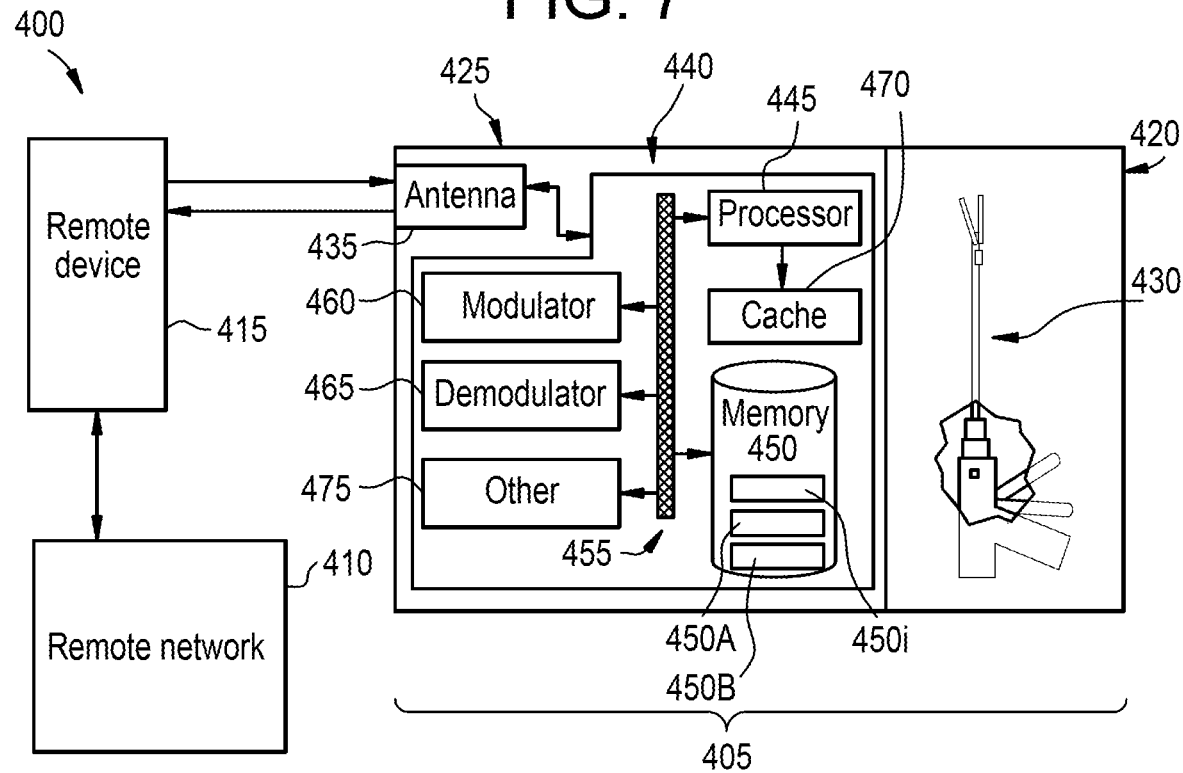
FIG. 7 is another diagram illustrating a radio frequency communication system including a medical device, a protective container having the medical device disposed therein, and an RFID tag disposed within the protective container.

FIG. 7 is a diagram illustrating a communication system 400 including a smart package assembly 405 and a remote network 410 communicatively coupled to at least one remote device 415. In some embodiments, the remote device 415 can include, but is not limited to, an RFID reader, an RFID beacon, or any other device that is configured to exchange data with the RFID tag as described herein, and can form one of the components of the "HUB" described above. The remote network 410 can be configured to exchange data with all of the remote device 415 as described in further detail below.

In some embodiments, the system 400 can include a plurality of remote devices 415 which form part of a remote device network installed at multiple places at a given location within the supply chain described above, which may comprise one or more of the components of the "HUB"

described elsewhere herein, and the one or more remote devices 415 can be communicatively coupled to the remote network 410.

In some embodiments, the remote network 410 can include a remote server system that is located at a facility that is different from that at which the remote device 415 is installed. In some embodiments, the remote device 415 can be configured to communicate with the remote network 410 over an external network (e.g., the internet). In other embodiments, the remote network 410 can include a site local server system located at the facility at which the remote device 415 is installed. In some embodiments, the remote device 415 can also be configured to communicate with the remote network 410 via a hard wired connection or via a wireless communication protocol.

As explained above, the smart package assembly 405 can include a protective container 420 and a radiofrequency identification (RFID) tag 425 disposed on or within the protective container 420. The protective container 420 can have a medical device 430 or other component disposed therein, and the protective container 420 can be sealed to prevent contaminates from contacting the medical device. In some embodiments, the RFID tag 425 can have a similar architecture as that of RFID tag 2 of FIG. 1, including an antenna 435 electronically coupled to an integrated circuit (IC) 440, both of which are mounted on a substrate (not shown).

In some embodiments, the RFID tag 425 can include a degradable/modifiable element that is designed to degrade over time. This can prevent old tags from being reused in counterfeit applications. For example, in some embodiments, the RFID tag 425 can be made using a plurality of strands of different polymers, each of which having a different degradation property (e.g., some of the polymers can be gamma sensitive, others humidity sensitive, others temperature sensitive, others light sensitive, etc. When the circuit is closed, it enables the RFID tag 425 to function. However, when one or more of the strands is exposed to the environmental factors it is sensitive to, it can be configured to break down, causing the circuit to be opened and disabling the RFID 425.

In some embodiments, the integrated circuit 440 can include at least one processor 445 and a memory 450 in operable communication with the processor 445. The memory 450 can store data characterizing instructions 450*i* that, when provided to the processor 445, cause the processor 445 to execute one or more processes in accordance with the instructions 450*i*. The memory 450 can also store a plurality of subsets of data 450A, 450B that can characterize one or more attributes of the medical device 430, the RFID tag 425 (including components thereof), and/or the protective container 420, as well as other aspects of the smart package assembly 405 and its constituent components described elsewhere in detail herein. Although the memory 450 is described herein as storing a plurality of subsets of data, in some embodiments the memory 450 can store a single set of data characterizing one or more of these attributes and/or aspects. Similarly, although the memory 450 is described as storing subsets of data 450A, 450B, in some embodiments the memory 450 can store additional subsets of data beyond the subsets of data 450A, 450B described herein. The memory 450 can be any device suitable for storing computer readable data. The memory can be a device with fixed storage or a device for reading removable storage media. Examples include all forms of non-volatile memory, media and memory devices, semiconductor memory devices (e.g., EPROM, EEPROM, SDRAM, flash memory devices, and all types of solid state memory), magnetic disks, and magneto optical disks. The integrated circuit can have any number of memory devices.

As illustrated in FIG. 7, the processor 445 is in communication, via a connection bus 455, with a modulator 460, a demodulator 465, and the memory 450. The processor 445 incorporates, or is directly connected to, a cache memory 470. The cache memory 470 is generally a form of high-speed computer memory placed in close proximity to the processor for fast read/write times. In some implementations, the cache memory 470 is part of, or on the same chip as, the processor 445. Processes that can be performed by the processor 445 can include, but are not limited to, determinations of exact subsets of data of the subsets of data 450A, 450B stored on the memory 450 to transfer to the remote device 415 via the antenna 435 as described in additional detail below. The processor 445 can be any logic circuitry that processes instructions, e.g., instructions fetched from the memory 450 or cache 470. In many embodiments, the processor 445 is an embedded processor, a microprocessor unit or special purpose processor. The integrated circuit 440 can be based on any processor, e.g., suitable digital signal processor (DSP), or set of processors, capable of operating as described herein. In some embodiments, the processor 445 can be a single core or multi-core processor. In some embodiments, the processor 445 can be composed of multiple processors.

The modulator 460 can be configured to convert digital data that is stored on the RFID tag into a radio frequency (RF) signal that can be transmitted by the antenna 435. In some embodiments, the modulator 460 can modulate the digital data stored it onto an RF carrier signal using a modulation technique such as amplitude modulation (AM), frequency modulation (FM), phase modulation (PM), or any other modulation technique known in the art. Alternatively, the demodulator 465 can be configured to convert the RF signal that is received by the antenna 435 into digital data. In some embodiments, the demodulator 465 can be configured to demodulate the received RF signal to extract the digital data by stripping the data from the RF carrier signal, using techniques such as amplitude demodulation, frequency demodulation, or phase demodulation, or any other known demodulation technique known in the art. In some embodiments, the modulator 460 and demodulator 465 can be integrated in the same circuit to form a singular modulation/demodulation modem.

In some embodiments, the IC 440 can further include other devices 475. Examples of other devices 475 include, but are not limited to: a power supply configured to store and supply power to the RFID tag, a power management component configured to manage power consumption of the RFID tag, encryption/decryption hardware configured to encrypt/decrypt data generated by and/or stored by the RFID tag to enhance the security of the RFID tag, a GPS device configured to determine location data characterizing the location of the tag, and/or sensors (e.g. a temperature sensor, an accelerometer, a magnetic sensor, a light sensor, etc.) to monitor the environment of the RFID tag and to generate data characterizing the environment in which the RFID tag is located. As explained above, the memory 450 can be configured to store data including, but not limited to, instructions 450*i* configured to cause the data processor 445 to perform one or more operations. And, as explained above, the memory 450 can also store data including plurality of subsets of data 450A, 450B pertaining to the smart package assembly 405 and/or the medical device 430 disposed therein. For example, the instructions 450*i* stored in the memory can include rules for transmission of data stored in the memory 450. In some embodiments, the instructions 450i can characterize data transfer rules defined based on the plurality of subsets of data, a level of power in a power source of the assembly, and data in the request data, which can include, for example, a query for a specific subset of the plurality of subsets of data, a location of the requesting remote device, an intended use of the requested data, etc. The plurality of subsets of data 450A, 450B can include, but are not limited to, a location of the assembly 405, a type of medical device 430 stored in the assembly 405, a historical log of the assembly 405 (e.g. previous locations or damage), and other forms of data characterizing the medical device. The data regarding the medical device 430 can include, for example, a historical log of usage statistics, previous failures, previous maintenance and/or replacements, previous interactions with other devices, etc. The data regarding the medical device 430 can also include a list of components of the device, an intended use for the device, and instructions on how to use the device.

As explained above, in some embodiments, the RFID tag 425 can be configured to receive request data from a remote device 415 in operable communication with the RFID tag 425. In some embodiments, the request data can include data characterizing a future data processing operation to be performed on the data requested, the data requested being in subsets 450A-450B. In some embodiments, for example, the request data can include a request for subset 450A, along with the future data processing operation. In this embodiment, the future data processing operation can include an intended use of the subset 450A to be transmitted. In some embodiments, the RFID 425 can be configured to determine the subset 450A based on the received request data and the future data processing operation. An example of a future data processing operation can include data characterizing an attribute that indicates that the subset of data 450A will be utilized in downstream computing operations required in response to issuance of a company Product Inquiry (PI). A PI issuance can be made, for example, in the event that multiple client reports received by a company have led to the company to decide that a specific product or component may need to be recalled. In the event of a PI, rather than pulling data from all of the packages and sending the company an excessive amount of data that has to be filtered upon receipt, the system 400 described herein allows for an automated and targeted acquisition of data based on what information is desired.

For example, in the event that it is determined that a particular wiring configuration in a surgical stapler made after a given date produces a detrimental misfire, the company can send out a PI. In some embodiments, the request data can further include a future data processing operation, in this case, the future data processing operation being a PI. In response to this PI, all remote devices 415 can be configured to query all smart package assemblies 405 in their vicinity as to whether or not they contain a surgical stapler, and if they were made after the given date. The smart package assemblies 405 can be configured to only respond to the query if they contain a surgical stapler and were made after the given date. This automated querying can provide the company with a concise list of smart package assemblies 405 of interest, which can in turn, aid in an efficient and targeted recall.

In some embodiments, the smart package assembly 405 can further include one or more separate return packages (not shown) for returning all or separate parts of the medical device 430 to various return locations as described in further detail below. In some embodiments, the return packages can be similar to the smart package assembly 405 and can be configured to operate similarly to the smart package assemblies described herein. In some embodiments, the return package could also be a non-smart package (e.g. a box and/or other simple container lacking the RFID functionality described herein). In some embodiments, the smart package assembly 405 can be configured to transfer operational data to the return package and appended the data to the data stored in the return package to be analyzed by a recipient of the return package.

In some embodiments, when the smart package assembly 405 is a return package, the flow of data can be reversed, and the remote device can be configured to transmit data (e.g. operational data) to the assembly 405. In this embodiment, the data transmitted to the assembly 405 can be appended to the data stored thereon (e.g. subsets of data 450A, 450B) to be analyzed upon return by a remote server (e.g. a server for the manufacturer of the medical device 630), as will be discussed in greater detail below.

In some embodiments, the request data can further include location data characterizing a location of the remote device 415 and/or the remote network, and, the response data can be determined based on the location data transmitted by the remote device 415. In some embodiments, the location data can originate from the remote network 410 from which the request data is received by the remote device characterized by the location data. In some embodiments, the location data can originate from the remote device 415 that is characterized by the location data. Location data can be an important aspect of the request data, as the data that is useful to any single point in the supply chain can differ greatly, and furthermore, data transfer protocols can vary depending on location. For example, in the event that a PI results in a product recall or product disposal, location data can be imperative, as return/reusability protocols can vary depending on the location of the smart package assembly 405 at any given point in the supply chain. For example, certain devices may not be able to be shipped via plane or other mode of transport depending on the location of the smart package assembly 405 at any given point in the supply chain. As another example, in the European Union, batteries in some devices may be required to be disposed of separately from the device, while in the United States, that may not be the case. Accordingly, in such an exemplary use of the functionality described above, a smart package assembly 405 could be sent to a country with data characterizing all possible return addresses for the smart package assembly 405 stored in the data thereon. Upon receipt of the smart package assembly 405 at a location at which the remote device 415 is installed, the return package could then be configured to receive the location data from the remote device 415 in the vicinity of the smart package assembly 405. Based on the location data included in the request data, the smart package assembly 405 could be configured to choose a return address from the possible return addresses in the event of a recall, based on a preprogrammed set of return rules.

Figure 8:
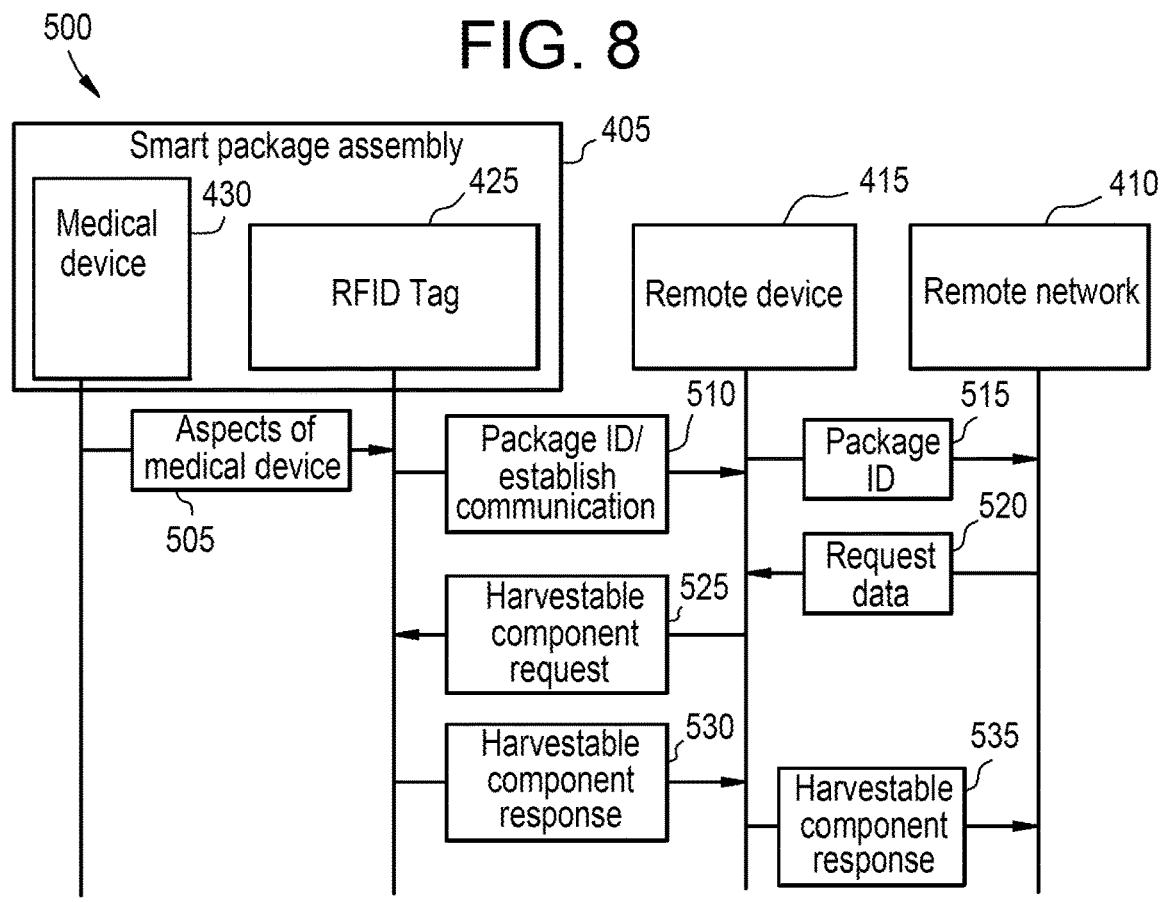
FIG. 8 is a flow diagram illustrating a data transfer interaction between components of the system of FIG. 7.

FIG. 8 is a diagram 500 illustrating an exemplary process for selectively adjustable data transfer between components of the smart package assembly 405 (e.g., the RFID tag 425 and/or the medical device 430), the remote device 415, and the remote network 410.

In some embodiments, the remote device 415 can be an RFID beacon, a hand-held RFID reader, another smart package assembly similar to assembly 405, or another type of remote device as described herein. In some embodiments, the remote network 410 can be a server system configured to communicatively couple a plurality of remote devices in a plurality of locations around the world. In some embodiments, the remote network 410 can further include the plurality of remote devices 415 configured to exchange data with a server system.

In some embodiments, when the medical device 430 is placed in the smart package assembly 405, the smart package assembly 405 can be configured to receive data, at 505, characterizing a history of use of the medical device 430 as well as a listing of reusable (harvestable) components of the medical device 430. In some embodiments, the historical data can include, for example, a past locations log, a past surgical operation log, a past failures log, a past maintenance log, etc. In some embodiments, the history of use data can further include defect data characterizing a defect of the medical device. In some embodiments, the smart package assembly 405 can be configured to receive the data characterizing the history of use of the medical device 430 and the listing of reusable components of the medical device 430 from the remote device 415. For example, in the event that the smart package assembly 405 is a return package for the medical device 430, the assembly 405 could be configured to receive the data characterizing a history of use of the medical device 430 as well as a listing of reusable (harvestable) components of the medical device 430 from an original smart package assembly used to originally ship the medical device 430. In some embodiments, the smart package assembly 405 can be configured to write the data received at 505 to the memory of the RFID tag 425 such that the device use data is included in the data stored in the memory of the tag 425.

In some embodiments, the RFID tag 425 can be configured to determine, from the data received at 505, reusable component data characterizing the listing of the reusable components of the medical device 430. In some embodiments, the reusable component data can be determined by cross-referencing the historical data previously stored in the memory of the package with the data received at 505. The reusable component data determined can include, for example, transection times of reusable components, number of transections, electrical data of reusable components, number of firings of reusable components, cartridges used in reusable components, number of surgeries performed by the device 430, surgical data from surgeries, etc.

The smart package assembly 405 can also be configured to be "self-aware". Accordingly, the RFID 425 can be configured to automatically determine whether or not it is in operable communication with a remote device 415 of a remote network 410 via data exchange 510. In some embodiments, the RFID 425 of the smart package assembly 405 can be configured to determine operable communication with the remote device 415 using a variety of RFID communication protocols including, but not limited to ISO 14443, ISO 15693, or EPC Gen2 protocols. In some embodiments, responsive to determining operable communication with the remote device 415 via data exchange 510, the RFID tag 425 of the smart package assembly 405 can be configured to transmit the data received at 505 to the remote device 415. In some embodiments, the RFID tag 425 can further be configured to transmit data regarding uniquely-identifying information about the smart package assembly 405 (e.g. serial number, past location checkpoints in the supply chain, etc.) along with the data received at 505. In some embodiments, the remote device 415 can be configured to transmit the data received at 510 to the remote network 410 at 515.

Responsive to receiving the data from the RFID tag 425 at 510 and/or 515, the remote device 415 and/or the remote network 410, respectively, can be configured to verify the authenticity of the data received. For example, in some embodiments, the remote device 415 and/or the remote network 410 can be configured to compare the data regarding the medical device 430 to the data regarding the smart package assembly 405 to ensure, for example, that the operational data, past location checkpoints, serial numbers, etc. match. In a case where a discrepancy is detected by the remote device 415 and/or the remote network 410, the remote device 415 and/or the remote network 410 can be configured to notify the manufacturer of a potential error or counterfeit. For example, in a case where the medical device 430 is a surgical stapler, there could be a situation where a surgeon uses the stapler with cartridges that are made by the manufacturer of the stapler, as well as with knock-off cartridges made by a third party. In this case the stapler, the RFID tag 425 and/or the remote device 415 can be configured to track how many cartridges that are made by the manufacturer were opened versus how many total cartridges were fired in the stapler. If there is a mismatch in the number of cartridges opened that are made by the manufacturer and the total number of cartridges fired, the manufacturer would be able to determine that knock-off cartridges were also used, which could be the reason for the failure in the stapler.

In some embodiments, the remote device 415 and/or the remote network 410 can be configured to communicate with the manufacturer/company over the internet. A manufacturer can verify the authenticity of the data received by the remote device 415 and/or the remote network 410 at 510, 515, respectively.

In some cases, the remote device 415 may not have internet access. Accordingly, in some embodiments, the remote device 415 can be configured to compare the data received at 510 to reference data stored locally on the device 415. For example, in a case where a remote device 415 does not have internet access, a user interacting with the remote device 415 can be configured to look up the serial numbers of the medical device 430 and/or the smart package assembly 405 on an external system to check for inconsistencies.

The authentication protocols described herein provide a system capable of detecting copies of legitimate data and not accepting such data. This is achieved by providing, in the data transmitted at 510, unique identification information, such as a unique serial number (S/N), batch code, or other authentication information that is specific to the medical device 430 and the smart package assembly 405. For example, in a case where data from an RFID tag 425 is written to a memory on a counterfeit tag, the remote device 415 and/or the remote network 410 will not verify the counterfeit tag.

In some embodiments, this authentication can be achieved using cryptographic techniques such as encryption and digital signatures to ensure that the tag is genuine. In this case, the smart package assembly 405 can use a cryptographic algorithm to generate a unique code based on stored data. The remote device 415 can then verify the authenticity of the smart package assembly 405 by comparing the received code to a reference stored on the remote device 415. This can provide an additional level of security and prevent tampering with the identifying information.

In some embodiments, this authentication can be achieved using the unique identifiers provided by the medical device 430 and/or RFID tag 425 of the smart package assembly 405, as described above, to determine whether or not the device and/or package is a duplicate.

In some cases, due to damage on the RFID tag 425 and/or other connectivity issues, the RFID tag 425 may not establish operable communication with a remote device 415. Accordingly, in some embodiments, the smart package assembly 405 can include a variety of secondary tags disposed thereon, configured to be recognized and validated by the remote device 415. For example, remote device 415 can include a camera sensor, an infrared sensor, and/or a magnetic sensor. In this case, the smart package assembly 405 can include a unique barcode, QR code, magnetic strip, etc. that can be detected by the camera sensor or a magnetic sensor. The smart package assembly 405 can also include a label printed in infrared invisible ink that can only be detected by the infrared sensor. In some embodiments, the smart package assembly 405 can include labels indicating a unique color, unique font, unique text size, unique word, unique letter, a missing pixel, etc. In some embodiments, the smart package assembly 405 can have a plurality of stamps disposed thereon, with only one printed in the correct font. This can help to prevent counterfeit production. Further, in some embodiments, the medical device 430 can have a physical identifier disposed thereon that can be recognized and interpreted by the remote device 415. For example, a medical device 630 can include a new component that has a "+" printed or otherwise marked on the component to indicate to a camera sensor of the remote device 415 that the component is a new model.

In some embodiments, the remote network 410 can be in charge of carrying out targeted data acquisitions from various remote devices 415 (e.g. in the form of a product inquiry). Accordingly, in some embodiments, the remote device 415 can be configured to receive request data, at 520, from the remote network 410. In some embodiments, the request data received at 520 can include a request for information about the package(s) 405 in communication with the remote device 415.

Responsive to the request data received at 520, the remote device 415 can be configured to transmit request data, at 525, to all or some of the packages 405 that have established operable communication with the remote device 415. In some embodiments, the request data received by the RFID tag 425, at 520 can include data characterizing the location of the remote device 415, along with an intended use of the requested data. The request data can also include a request for any of the data received by the smart package assembly 405 from the medical device 430 at 505. The assembly 405 can be configured to receive the request, and compare the request data to data stored thereon characterizing the smart package assembly's 405 actual and/or future location, the medical device's 430 intended use, medical device 430 specifications, and/or power level of the smart package assembly 405 (if powered by a power supply), and the like. The processor can be configured to determine the subset of the data to be transmitted based on the results of the comparison, and respond to the request with the subset of the data.

In some embodiments, the request data received at 525 can include a request for the reusable component data determined above. In some embodiments, the request data received at 520 can include a request for the data characterizing the number of surgeries performed by the device 430 and/or surgical data from the surgeries received at 505.

In some embodiments, after a surgical procedure using medical device 430, remote device 415 can be configured to determine the reusable parts of the device 430 and query the device 430 and/or package 405, at 525, to determine if the parts are still harvestable following procedure. The medical device 430 can be configured to transmit a response to the remote device 415 and/or the remote network 410, at 530, 535, respectively. In the event where parts are still harvestable, the remote network 410 can be configured to coordinate steps for harvest. In some embodiments, the harvest ability of initially harvestable components could depend on the component's age/expiration date, wear and tear, number of procedures completed, repairs or maintenance that have been performed on it, etc. Wear and tear data can be acquired by a variety of sensors coupled to the medical device 430. Some sensors that could be used can include, for example, accelerometers to track the movement and vibration of a medical device 430 during use. Load cells could also be used to monitor the load on the medical device 430 or its components. Temperature sensors could also be used to monitor the temperature of the device 430 and/or its components, and humidity sensors could be used to monitor the moisture content in the environment around the medical device 430. Confirming harvestability based on wear and tear can include registering, by the smart package assembly 405, anomaly events reported by the sensors coupled to the medical device 430 and communicating those anomaly events to the smart package assembly 405 and/or to the remote network 410 via the remote devices 415 with corresponding timestamps. In some embodiments, harvestability can be determined by using a variety of transducers disposed within the medical device 430 and/or the package assembly 405.

In some embodiments, the steps for harvest can include inserting the component into return packaging, cleaning the component, verifying the return shipment information, biohazard handling, etc. In some embodiments, the smart package assembly 405 can include data characterizing a date manufactured and/or an expiration data. In this embodiment, confirming harvestability based on age can simply include comparing, by the smart package assembly 405 and/or the remote network 410, a current date to data characterizing an expiration date of the component.

In some embodiments, as discussed above, the smart package assembly 405 can be a return package configured for use in returning the medical device 430, or a component thereof, to the manufacturer. In this case, the flow of data described above can be reversed. For example, in a case where the medical device 430 was just used during an operation, the remote device 415 can be configured to store operational data regarding the operation. In this case, the remote device 415 can be configured to transmit operational data from the most recent operation to the RFID tag 425 at 525. The operational data transferred at 520 can include, but is not limited to a surgeon report of the operation, and operational data tracked by other devices and systems used in the operation. In some embodiments, the operational data can also include defect data characterizing a defect in the medical device 430 and/or a component thereof. In some embodiments, the operational data can also include reusable component data including, for example, transection times of reusable components, number of transections of reusable components, electrical data of reusable components, number of firings of reusable components, cartridges used in reusable components, number of surgeries performed by the device 430, surgical data from surgeries, etc.

For example, in the event that a surgeon reports a failure with the surgical stapler, the remote device 415 can be configured transmit that report to the RFID tag 425. When the smart package assembly 405 is returned to the manufacturer, the operational data that is transmitted to the RFID tag 425 can then be transmitted to a remote server (not shown, e.g., a server used by the manufacturer of the medical device 630). The data transmitted to the remote server (also referred to as a recipient server herein) can be used by the manufacturer to investigate the failure. In some embodiments, the medical device 430 can also be configured to transmit operational data tracked by the medical device 430 during the operation to the RFID tag 425. In some embodiments, the remote server can be in operable communication with the remote network 410. In this case, the surgeon report data and other operational data can be transmitted, via the remote device 415 to the remote network 410, and further to the remote server for future analysis, including cross-referencing by the manufacturer to ensure that no discrepancies exist. For example, if the surgeon indicates in the surgeon report data that a component of the stapler was broken during the shipping process or has a manufacturing defect, the operational data can be used to validate/invalidate that claim. If, for example, a component of the stapler is broken, but no anomaly event was reported from one or more sensors configured to monitor the component, then it can be determined that the component was in fact broken during the shipping process or has a manufacturing defect. Alternatively, for example, if the component is broken, and data characterizing activations of the stapler when the stapler was checked in for surgery overlaps with data characterizing an anomaly event, then it can be determined that the component was broken during a surgical operation. In the event that it is determined that the component was broken during surgery, the operational data can be investigated further to identify how the damage occurred.

There are several technical advantages of a smart package assembly that is capable of providing automatic, selective data transmission based on the intended use of the data by the requesting system and/or the location of the requesting system. Technical advantages can include improved data security, improved supply chain coordination, and overall increased system efficiency.

By selectively transmitting data to external requesting systems based on the intended use of the data, the smart package assembly described herein can improve data security by preventing sensitive information from being shared with unauthorized parties and/or malicious actors. This can reduce the risk of data breaches and other security incidents. The selective data transmission based on intended use, as described herein, further provides a smart package assembly capable of helping businesses to comply with regulatory and industry requirements related to data security and privacy. By transmitting data only to trusted external requesting systems, and only for specify intended uses, the system described herein can reduce the risk of non-compliance with relevant regulations and standards. This can help businesses to avoid falling out of compliance, and to increase the protection of sensitive data.

As mentioned above, the systems described herein can further provide the technical advantage of improving supply chain coordination and overall system efficiency. The self-aware smart package assembly described herein is advantageously capable of ensuring that only data relevant the current point in the supply chain is provided to requesting devices at that point in the supply chain. Additionally, selective data transmission based on intended use can further help reduce data transfer volume by transmitting only the necessary data to external requesting systems, rather than transmitting all data stored in the system, which can improve efficiency.

Operational Data and Executable Code

Accordingly, the present disclosure provides a smart package assembly capable of providing automatic transmission of executable code from a smart package assembly to a requesting system via radio frequency waves using RFID technology. The smart package assembly described herein can be configured to receive request data characterizing a query for an electronic identifier corresponding to a medical device, or component thereof stored within the smart package assembly. The received query data can be used by the smart package assembly to determine program data characterizing executable instructions configured to cause a remote processor to perform operations for determining an the electronic identifier. In another example, the smart package assembly described herein can be configured to receive request data characterizing a query for operational data characterizing at least one control parameter for operating the medical device, the operational data forming part of the first data stored in the memory. The operational data can be used, for example, to provide a more detailed insight of the device's operations. This can help, for example, in validating a surgeon's description of events that occur during a surgical operation. The transference of program data afforded by the present disclosure can advantageously enable a medical device packaging assembly to autonomously inform a requesting system and or a remote network of any instructional or software updates that may be needed to interact with the medical device disposed therein. Further, the transference of operational data afforded by the present disclosure can advantageously enable a medical device packaging assembly to autonomously inform a requesting system and or a remote network of any operational anomaly events or other important operational information to aid in operational optimization.

Figure 9:
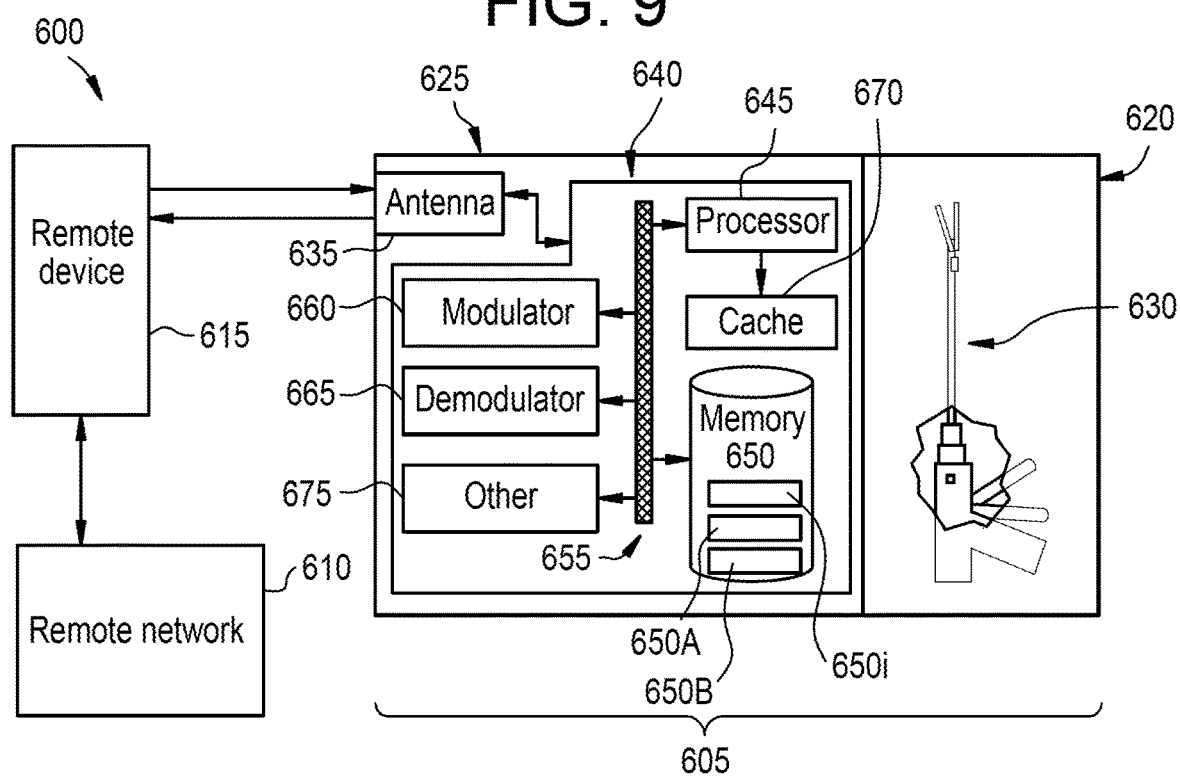
FIG. 9 is another diagram illustrating a radio frequency communication system including a medical device, a protective container having the medical device disposed therein, and an RFID tag disposed within the protective container.

FIG. 9 is a diagram illustrating a communication system 600 including a smart package assembly 605 and a remote network 610 communicatively coupled to at least one remote device 615. In some embodiments, the remote device 615 can include, but is not limited to, an RFID reader, an RFID beacon, or any other device that is configured to exchange data with the RFID tag as described herein, and can form one of the components of the "HUB" described above. The remote network 610 can be configured to exchange data with all of the remote device 615 as described in further detail below.

In some embodiments, the system 600 can include a plurality of remote devices 615 which form part of a remote device network installed at multiple places at a given location within the supply chain described above, which may comprise one or more of the components of the "HUB" described elsewhere herein, and the one or more remote devices 615 can be communicatively coupled to the remote network 610.

In some embodiments, the remote network 610 can include a remote server system that is located at a facility that is different from that at which the remote device 615 is installed. In some embodiments, the remote device 615 can be configured to communicate with the remote network 610 over an external network (e.g., the internet). In other embodiments, the remote network 610 can include a site local server system located at the facility at which the remote device 615 is installed. In some embodiments, the remote device 615 can also be configured to communicate with the remote network 610 via a hard wired connection or via a wireless communication protocol.

As explained above, the smart package assembly 605 can include a protective container 620 and a radiofrequency identification (RFID) tag 625 disposed on or within the protective container 620. The protective container 620 can have a medical device 630 or other component disposed therein, and the protective container 620 can be sealed to prevent contaminates from contacting the medical device. In some embodiments, the RFID tag 625 can have a similar architecture as that of RFID tag 2 of FIG. 1, including an antenna 635 electronically coupled to an integrated circuit (IC) 640, both of which are mounted on a substrate (not shown).

In some embodiments, the RFID tag 625 can include a degradable/modifiable element that is designed to degrade over time. This can prevent old tags from being reused in counterfeit applications. For example, in some embodiments, the RFID tag 625 can be made using a plurality of strands of different polymers, each of which having a different degradation property (e.g., Some of the polymers can be gamma sensitive, others humidity sensitive, others temperature sensitive, others light sensitive, etc. When the circuit is closed, it enables the RFID tag 625 to function. However, when one or more of the strands is exposed to the environmental factors it is sensitive to, it can be configured to break down, causing the circuit to be opened and disabling the RFID 625.

In some embodiments, the integrated circuit 640 can include at least one processor 645 and a memory 650 in operable communication with the processor 645. The memory 650 can store data characterizing instructions 650*i* that, when provided to the processor 645, cause the processor 645 to execute one or more processes in accordance with the instructions 650*i*. The memory 650 can also store a plurality of subsets of data 650A, 650B that can characterize one or more attributes of the medical device 630, the RFID tag 625 (including components thereof), and/or the protective container 620, as well as other aspects of the smart package assembly 605 and its constituent components described elsewhere in detail herein. Although the memory 650 is described herein as storing a plurality of subsets of data, in some embodiments the memory 650 can store a single set of data characterizing one or more of these attributes and/or aspects. Similarly, although the memory 650 is described as storing subsets of data 650A, 650B, in some embodiments the memory 650 can store additional subsets of data beyond the subsets of data 650A, 650B described herein. In some embodiments, the subsets of data 650A, 650B can be in a compressed form, as discussed in greater detail below. The memory 650 can be any device suitable for storing computer readable data. The memory can be a device with fixed storage or a device for reading removable storage media. Examples include all forms of non-volatile memory, media and memory devices, semiconductor memory devices (e.g., EPROM, EEPROM, SDRAM, flash memory devices, and all types of solid state memory), magnetic disks, and magneto optical disks. The integrated circuit can have any number of memory devices.

As illustrated in FIG. 9, the processor 645 is in communication, via a connection bus 655, with a modulator 660, a demodulator 665, and the memory 650. The processor 645 incorporates, or is directly connected to, a cache memory 670. The cache memory 670 is generally a form of high-speed computer memory placed in close proximity to the processor for fast read/write times. In some implementations, the cache memory 670 is part of, or on the same chip as, the processor 645. Processes that can be performed by the processor 645 can include, but are not limited to, determinations of exact subsets of data of the subsets of data 650A, 650B stored on the memory 650 to transfer to the remote device 615 via the antenna 635 as described in additional detail below. The processor 645 can be any logic circuitry that processes instructions, e.g., instructions fetched from the memory 650 or cache 670. In many embodiments, the processor 645 is an embedded processor, a microprocessor unit or special purpose processor. The integrated circuit 640 can be based on any processor, e.g., suitable digital signal processor (DSP), or set of processors, capable of operating as described herein. In some embodiments, the processor 645 can be a single core or multi-core processor. In some embodiments, the processor 645 can be composed of multiple processors.

The modulator 660 can be configured to convert digital data that is stored on the RFID tag into a radio frequency (RF) signal that can be transmitted by the antenna 635. In some embodiments, the modulator 660 can modulate the digital data stored it onto an RF carrier signal using a modulation technique such as amplitude modulation (AM), frequency modulation (FM), phase modulation (PM), or any other modulation technique known in the art. Alternatively, the demodulator 665 can be configured to convert the RF signal that is received by the antenna 635 into digital data. In some embodiments, the demodulator 665 can be configured to demodulate the received RF signal to extract the digital data by stripping the data from the RF carrier signal, using techniques such as amplitude demodulation, frequency demodulation, or phase demodulation, or any other known demodulation technique known in the art. In some embodiments, the modulator 660 and demodulator 665 can be integrated in the same circuit to form a singular modulation/demodulation modem.

In some embodiments, the IC 640 can further include other devices 675. Examples of other devices 675 include, but are not limited to: a power supply configured to store and supply power to the RFID tag, a power management component configured to manage power consumption of the RFID tag, encryption/decryption hardware configured to encrypt/decrypt data generated by and/or stored by the RFID tag to enhance the security of the RFID tag, a GPS device configured to determine location data characterizing the location of the tag, and/or sensors (e.g. a temperature sensor, an accelerometer, a magnetic sensor, a light sensor, etc.) to monitor the environment of the RFID tag and to generate data characterizing the environment in which the RFID tag is located. As explained above, the memory 650 can be configured to store data including, but not limited to, instructions 650*i* configured to cause the data processor 645 to perform one or more operations. And, as explained above, the memory 650 can also store data including plurality of subsets of data 650A, 650B pertaining to the smart package assembly 605 and/or the medical device 630 disposed therein. For example, the instructions 650*i* stored in the memory can include rules for transmission of data stored in the memory 650. In some embodiments, the instructions 650*i* can characterize data transfer rules defined based on the plurality of subsets of data, a level of power in a power source of the assembly, and data in the request data, which can include, for example, a query for a specific subset of the plurality of subsets of data, a location of the requesting remote device, an intended use of the requested data, etc. The plurality of subsets of data 650A, 650B can include, but are not limited to, program data including instructions on how to use the medical device 630, and executable code configured to be run by the receiving remote device 615. In some embodiments the executable code can be configured to calibrate the remote device 615 for use with the medical device 630. The plurality of subsets of data 650A, 650B can also include a historical log operational data of the medical device 630 and/or previous locations and/or damage to the smart package assembly 605 or the medical device 630. In some embodiments the operational data can include a log of usage statistics, compatibility data, previous anomaly events, previous maintenance and/or replacements, previous interactions with other devices, and/or any other important surgical data. The data regarding the medical device 630 can also include a list of components of the device, and an intended use for the medical device 630.

As explained above, in some embodiments, the RFID tag 625 can be configured to receive request data from a remote device 615 in operable communication with the RFID tag 625. In some embodiments, the request data can include data characterizing a query for a subset of the data stored in the memory to be provided to the remote device (e.g., 650A or 650B). In some embodiments, the request data can include data characterizing a request for instructions on how to use the device 630, information regarding a past surgical operation(s), a necessary software update to ensure compatibility with the device 605, etc.

In some embodiments, the plurality of subsets of data 650A or 650B can be used, for example, to aid in a company Product Inquiry (PI). Issuance of a PI can be made, for example, in the event that multiple client reports received by a company have led to the company to decide that a specific product or component may need to be recalled. In the event of a PI, the system described herein allows for an automated and targeted acquisition of data based on what information is desired. For example, in the event that multiple errors/failures of a given medical device 605 have been reported by surgeons using the devices, a PI can be made to acquire operational data for a plurality of medical devices 605. In this case, the operational data can be used to interrogate error/failure events to learn more about the environments in which they occur, and to cross-reference the operational data with the surgeons' claims, to understand if the errors/failures are device related, or user related, as will be discussed in greater detail below.

Packages can be configured to receive anomaly sensor data from a variety of sensors within a device as the plurality of subsets of data 650A or 650B. Sensor data can be received by microphones or other sensors to detect changes in sound or vibration that may indicate contact with metal or any other hard material. Sensor data can also be received by cameras or other optical sensors to detect changes in light or color that may indicate contact with metal any other hard material. Sensor data can also be received by force sensors to detect anomaly events that may indicate harmful contact. Other sensors may also be used, and this data can also be recorded along with corresponding time stamps. Using this variety of sensor data, details of a surgical operation can be determined from the operational data including, but are not limited to, determining that a device was abused, which component (e.g. which cartridge of a stapler) was being used. If a blade or other component of a medical device broke during a surgical operation, additional details that can be determined from the operational data can include whether or not the blade or other component contacted metal or any other hard material during an operation based on anomalies present in the data. Additionally, if electrical short occurred, the data can be used to determine whether it was it a long term short and/or whether it occurred in the middle of an operation. Furthermore, if electrical short occurred, sensor data can be used to diagnose the cause (e.g. a fluid ingress observed via a sensor).

In some embodiments, the smart package assembly 605 can further include one or more separate return packages (not shown) for returning all or separate parts of the medical device 630 to various return locations as described in further detail below. In some embodiments, the return packages can be similar to the smart package assembly 605 and can be configured to operate similarly to the smart package assemblies described herein. In some embodiments, the return package could also be a non-smart package (e.g. a box and/or other simple container lacking the RFID functionality described herein). In some embodiments, the smart package assembly 605 can be configured to transfer operational data to the return package and appended the data to the data stored in the return package to be analyzed by a recipient of the return package.

In some embodiments, when the smart package assembly 605 is a return package, the flow of data can be reversed, and the remote device can be configured to transmit data (e.g. operational data) to the assembly 605. In this embodiment, the data transmitted to the assembly 605 can be appended to the data stored thereon (e.g. subsets of data 650A, 650B) to be analyzed upon return by a remote server (e.g. a remote server for the manufacturer of the medical device 630), as will be discussed in greater detail below.

Figure 10:
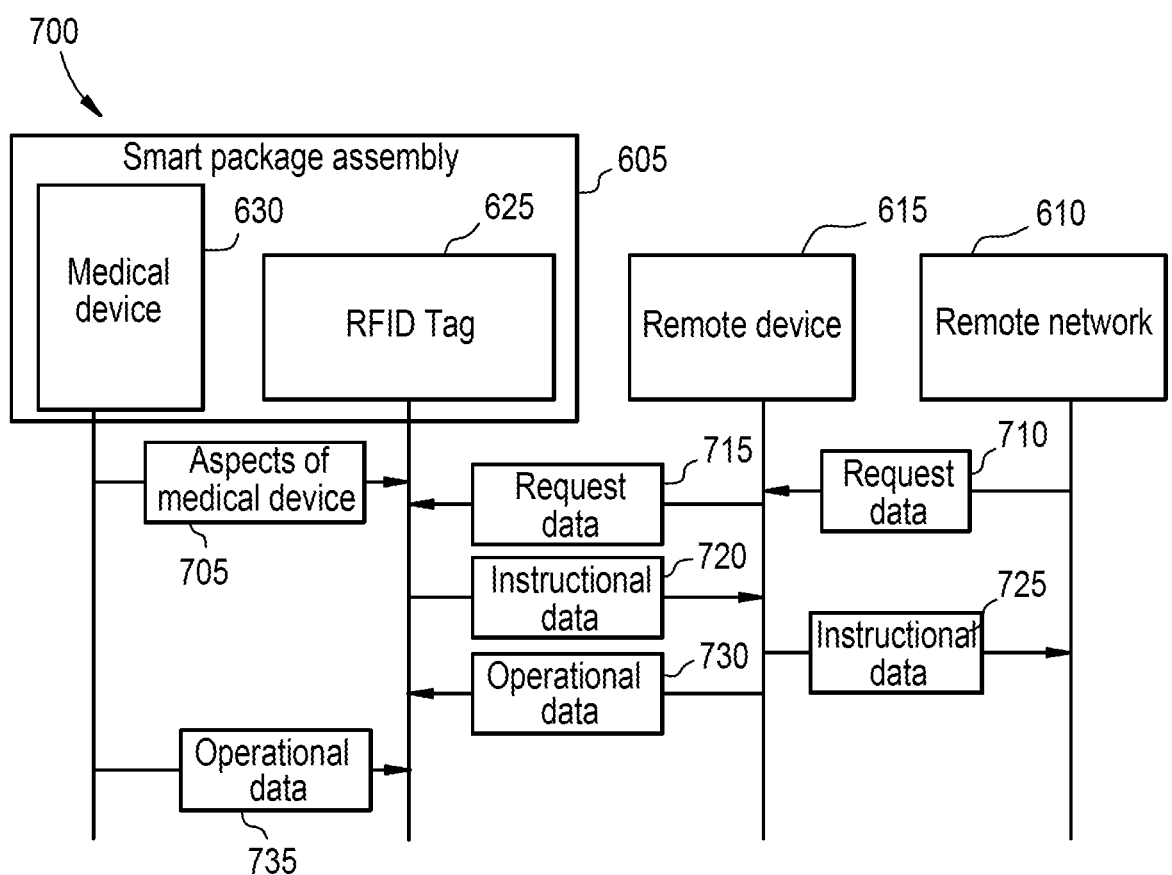
FIG. 10 is a flow diagram illustrating an exemplary process for transfer of executable code between components of the system of FIG. 9.

FIG. 10 is a diagram 700 illustrating an exemplary process for automatic transmission of operational data of a medical device 630, compatibility data of the medical device 630, instructional data, and/or executable code between components of the smart package assembly 605 (e.g., the RFID tag 625 and/or the medical device 630), the remote device 615, and/or the remote network 610.)

In some embodiments, the RFID tag 625 can, at 705, receive data characterizing one or more aspects of the medical device 230. For example, in some embodiments, the received data can include data characterizing a past surgical operation(s), compatibility data, instructional data, and/or executable code, as will be discussed in greater detail below. In some embodiments, the data received at 705 can comprise a part of the plurality of subsets of data 650A, 650B (in reference to FIG. 9).

In some embodiments, the remote network 610 can, at 710, transmit request data to the remote device 615, and the remote device 615 can, at 715, transmit the request data to the smart package assembly 605. In some embodiments, the request data can include data characterizing a query for the data stored in the memory 650 of the RFID tag 625, as will be discussed in greater detail below. In some embodiments, the remote network 610 can transmit data characterizing an instruction to the remote device 615 to cause the remote device 615 to transmit the request data.

In response to receiving the request data, the processor 645 of the RFID tag 625 can use the request data and/or instructions stored on the memory 650 of the RFID tag 625 to determine response data that it will transmit to the remote device 615, and, at 720, the response data can be transmitted from the RFID tag 625 to the remote device 615, as will be discussed in greater detail below. The remote device 615 can, at 725, transmit the response data to the remote network 610 for further processing by other electronic components in operable communication with the remote network 610, as will also be discussed in greater detail below.

In some embodiments, the operational data, compatibility data, instructional data, and/or executable code that is transmitted from the medical device 630 to the tag 625 at 705 can include large amounts of data, while the data storage capabilities of the RFID 625 and/or of the medical device 630 stored in the assembly 605 can be limited. Accordingly, as mentioned above, it can be advantageous for the data that is transmitted to the RFID 625 and stored thereon to be compressed in a variety of ways. The processor of the RFID tag 625 can be configured to redact unimportant data and/or compress data in order to increase storage capability and/or lessen the amount of data to be transferred to/from the RFID tag 625. Additionally, the remote device 615 can have a limited bandwidth—in which case compressed and/or refined data transmission can be desirable. Accordingly, the RFID 625 can be configured to only record data that is "important". "Important" data can include anomaly event data including, but not limited to, medical device 630 errors/failures, location checkpoints, assembly 605 damage, etc. All other data can be determined to be "unimportant" and can be marked as redacted to limit the amount of data stored on the memory 650. Unimportant data can include, for example, data characterizing operational data of the medical device 630 stored on the memory 650 of the RFID tag 625 and/or on the medical device 630 that is within an operational range.

The RFID 625 can also be configured to utilize data compression processes to allow for greater storage capability and to allow for more efficient data transmission to the remote device 615 in the event that the remote device 615 has limited bandwidth. Data compression can be achieved by simply deleting or truncating the data, replacing stings of data with simple characters to identify that something was redacted, or by using several data compression algorithms. Examples of data compression algorithms that can be used can include, but not be limited to: Lempel-Ziv-Welch (LZW) or Lempel-Ziv 77 (LZ77) compression, Huffman coding compression Run-length encoding compression, Arithmetic coding compression, and/or Deflate data compression. Accordingly, in some embodiments, the response data transmitted can be determined based on an amount of available bandwidth of the remote device 615. In some embodiments, the response data transmitted can also be compressed responsive to determining, by the remote device 615, that the amount of available bandwidth of the remote device 615 is less than a predetermined threshold.

In some embodiments, the data is stored on the RFID tag 625 can be compressed down to a simple electronic identifier (e.g. a variable length serial number) corresponding to the type of data that is embedded in the compressed data. In some embodiments, each character or series of characters can be configured to represent some component of a predetermined mini language syntax that can be identified by the remote device 615 and acted upon. In some embodiments, when requesting data from the assembly 605, the remote device 615 can be configured to send request data at 715 characterizing a query for the simple electronic identifier, which can then be interpreted in a variety of ways by the remote device, as will be described in greater detail below.

In some embodiments, when data is stored on the RFID tag 625 in a compressed form, the compressed data can include an electronic identifier (e.g. a variable length serial number) that characterizes one or more attributes of the compressed data. In this case, the electronic identifier can correspond to the type of data that is embedded in the compressed data. The electronic identifier can include metadata that describes the contents of the compressed data. This metadata can include information such as a data format, a file type, a type of medical device 630, a type of surgical operation or a brief description of the compressed data stored therein (e.g. software update data, configuration data, device compatibility data, etc.). In some embodiments, when requesting data from the assembly 605, the remote device 615 can be configured to send request data at 715 characterizing a query for a specific electronic identifier corresponding to a desired to of information stored on the RFID tag 625 or the medical device 630 in a compressed form, as discussed in greater detail below.

As discussed above, the RFID tag 625 can, at 705, receive data characterizing one or more aspects of the medical device 630. While, as illustrated in FIG. 10, in some embodiments the data characterizing one or more aspects of the medical device 630 can be received, at 705, from the medical device 630, in some embodiments, this data can be received from a separate device (not shown). The received data can include compatibility data for determining compatibility of the device 630 with other devices and/or systems. The received data can also include operational data of the medical device 630, and/or data characterizing a listing of reusable (harvestable) components. The received data can also include data characterizing instructions for how to use the medical device 630 (e.g. in the form of written instructions, an audio file, a video file or other graphical media, etc.) and/or executable code to be used by the remote device 615. In some embodiments, the data characterizing instructions and/or executable code can be used in combination with the compatibility data and/or the operational data, as will be described in greater detail below. Further, in some embodiments, the received data can include data can simply include an electronic identifier, as described above that can be interpreted in a variety of ways by the remote device 615. In some embodiments, the operational data can include data from past surgical operations, including but not limited to, a past errors/failures log, a past maintenance log, etc. In some embodiments, the instructional data can include written instructions and/or compressed video/audio tutorial files as described in further detail below. In some embodiments, the executable code can include software updates or other code that, when run by the remote device 615, properly configure or initialize the remote device 615 for use with the medical device 630. The received data can comprise a part of the plurality of subsets of data 650A, 650B.

As described above, the data received by the RFID tag 625 from the medical device 630 at 705 can include compatibility data and/or electronic identifiers configured to represent the compatibility data. The compatibility data can also include information regarding the specific device(s) with which the medical device 630 needs to be compatible. Compatibility data can be used to configure a device 630 to work with other devices. For example, a device 630 may need to be configured with the correct settings (e.g. control parameter, as discussed above) or protocols in order to communicate with another device. Compatibility data can also be used to integrate different medical devices (including medical device 630) into a single system. This can allow for the devices to share information and work together more seamlessly, improving the overall efficiency and effectiveness of the system.

In one example, the medical device 630 could include a surgical stapler. In this example, the stapler could be compatible with a variety of competitor's trocars, but at the time of manufacturing and/or shipping, it may have been unknown which trocar the stapler 630 would be used in combination with. Accordingly, to save time, the RFID tag 625 of the smart package assembly 605 can include a plurality of compatibility data (in some cases compressed) for a variety of competitor trocars. Alternatively, in some embodiments, the compatibility data can be compressed all the way down to unique, variable length electronic identifiers corresponding to the compatibility data. At the time of arrival at a destination operating room, the RFID tag 625 of the smart package assembly 605 can be configured to receive trocar information either directly from the competitor trocar or from another remote device 615 as a component of the request data at 715, along with a query for appropriate compatibility data. Responsive to the request, the RFID tag 625 can be configured to determine the proper compatibility data to transmit at 720 based on the specific information about the competitor trocar.

The data received by the RFID tag 625 from the medical device at 705 can also include a plurality of instructional data and/or executable code (in a compressed form, as discussed above) configured to be run by the remote device 615 and/or directly by another medical device. In some embodiments, the instructional data and/or executable code can include tutorial video, audio, or image files configured to inform a user of the proper use of the medical device 630. Alternatively, in some embodiments, the instructional data and/or executable code can be represented by a plurality of unique, variable length electronic identifiers that can be interpreted by the remote device 615 using a predefined mini language syntax, or the like.

For example, in some embodiments, the instructional data and/or executable code can be represented by an electronic identifier, such as a unique series of bits that represent a link to a video or code file or the like that is stored elsewhere (e.g. the internet). In this case, the electronic identifier would operate similarly to a barcode or a QR code or the like, but would be communicated to the remote device 615 using RF communication.

In some embodiments, the instructional data and/or executable code can include executable code configured to correct an operation of the medical device 630. The instructional data and/or executable code can also include executable code configured to calibrate and/or initialize a remote device 615 or other device for use with the medical device 630. In some embodiments, the calibration/initialization code can be a software update. Similarly to as discussed above, in some embodiments, the instructional data and/or executable code can be stored on another device or system (e.g. the internet) and the instructional data and/or executable code can be represented by an electronic identifier, such as a unique series of bits that represent a link to a video or code file or the like that is stored elsewhere. In this case, the electronic identifier would operate similarly to a barcode or a QR code or the like, but would be communicated to the remote device 615 using RF communication.

For example, if the medical device 630 is a new model, and it requires a new type of software to operate, the package assembly 605 could be configured to store the necessary software update and/or configuration data for the system that the device 630 will be interacting with thereon. In this case, upon arrival of the smart package assembly 605 at the destination location, the request data transmitted at 715 can include a request for compatibility data stored on the RFID tag 625 regarding the compatibility of the medical device 630 with various other devices or systems. In some embodiments, the request data can simply include request data indicating whether or not the device 630 is compatible with a device indicated in the request data. If it is determined that the device 630 is not compatible with the various other devices or systems due to the various other devices or systems having an outdated version of the software. In this case, the package can be configured to transmit, at 720, the software update and/or configuration data to the remote device 615 in the operating room. The software update and/or configuration data can then be used to update the various other devices or systems accordingly. In some embodiments, the RFID tag 625 can be configured to transfer the determined software update and/or configuration data or corresponding electronic identifier directly to the other device/system when placed in the vicinity of the device/system. In this case, the receiving device/system can be configured to decompress the data and begin a configuration process by running the executable code thereon.

Further, in some embodiments, the data transmitted at 720 can include additional instructions for how to properly calibrate the medical device 630 with the other device or system, so that the medical device 630 and the other device/system can operate together effectively. In some embodiments, the additional instructions can include instructions regarding an installation method, a calibration procedure, an initialization process, etc.

For example, responsive to transmitting the software update and/or configuration data to the remote device 615 at 720, the remote device 615 can be configured to transmit a second request at 715 characterizing a query for graphical/audio media or an electronic identifier thereof stored on the RFID tag 625. In some embodiments, the graphical/audio media can characterize a graphical/audio depiction of an operation as discussed above. In some embodiments, the graphical/audio media or electronic identifier thereof can include compressed data characterizing, for example, a video, an audio, or an image that acts as an informative tutorial for how to use the medical device 630 in view of the software update. Once received by the remote device 615 in the response data transmitted at 720, the remote device 615 can be configured to decompress the compressed data to view the video, audio, or image. Alternatively, the graphical/audio media can be represented by an electronic identifier, such as a unique series of bits that represent a link to a video or code file or the like that is stored elsewhere (e.g. the internet). In this case, the electronic identifier would operate similarly to a barcode or a QR code or the like, but would be communicated to the remote device 615 using RF communication. As mentioned above, the video, audio, or image can be directed toward an instructional tutorial regarding how to prepare, initialize, and/or calibrate the device 630 for use, or the like.

Further, in some embodiments, the request data transmitted at 715 can include a request for device usage data characterizing a frequency of use of the medical device 630. In some embodiments, the device usage data can further be associated with a specific user of the medical device 630, and can characterize an amount of use of the medical device 630 by the specific user. In some embodiments, the graphical/audio media or electronic identifier thereof to be transmitted to the remote device 615 at 720 can be determined by the smart package assembly 605 based on the device usage data and/or the associated user. For example, in the event that a particular user has used the device more than a predetermined amount of times with the new software update, the smart package assembly 605 can be configured to transmit a shortened or simpler instructional tutorial, or can be configured to not send an instructional tutorial at all.

As described above, other operating systems or devices can be configured to operate with the device 630. In some cases, the other operating systems or devices may be competitor devices. Accordingly, in some embodiments, the smart package assembly 605 and/or the medical device 630 can be configured to collect data from the other operating systems or devices that are communicatively coupled to the medical device 630, and store the date on the memory of the device 630. The data collected from competitor devices can include, but is not limited to operational data, component data, manufacturer, etc. In some embodiments, the data collected by the medical device 630 can be transmitted to the RFID tag 625 at 705. In some embodiments, the data collected by the device 630 regarding other operating systems or devices can be used by the RFID tag 625 to determine the proper executable code to correct a potential issue.

For example, if device chatter is observed in the device 630, which can indicate a hemostasis issue in a patient, the request data transmitted at 715 can characterize a query for a chatter operational parameter, and can include information about the other operating systems or devices being used with the device 630, that are in operable communication with the remote network 610. In this case, responsive to the query, the RFID tag 625 can be configured to determine and transmit, at 720, executable code, or an electronic identifier thereof to the remote device 615. The remote device 615 can, at 725, transmit the executable code to the remote network 610 to run the executable code on the operating system or other device configured to control the medical device 630. In some embodiments, the executable code can cause the operating system or other device to modify a power output to the medical device 630 to help control hemostasis.

Figure 11:
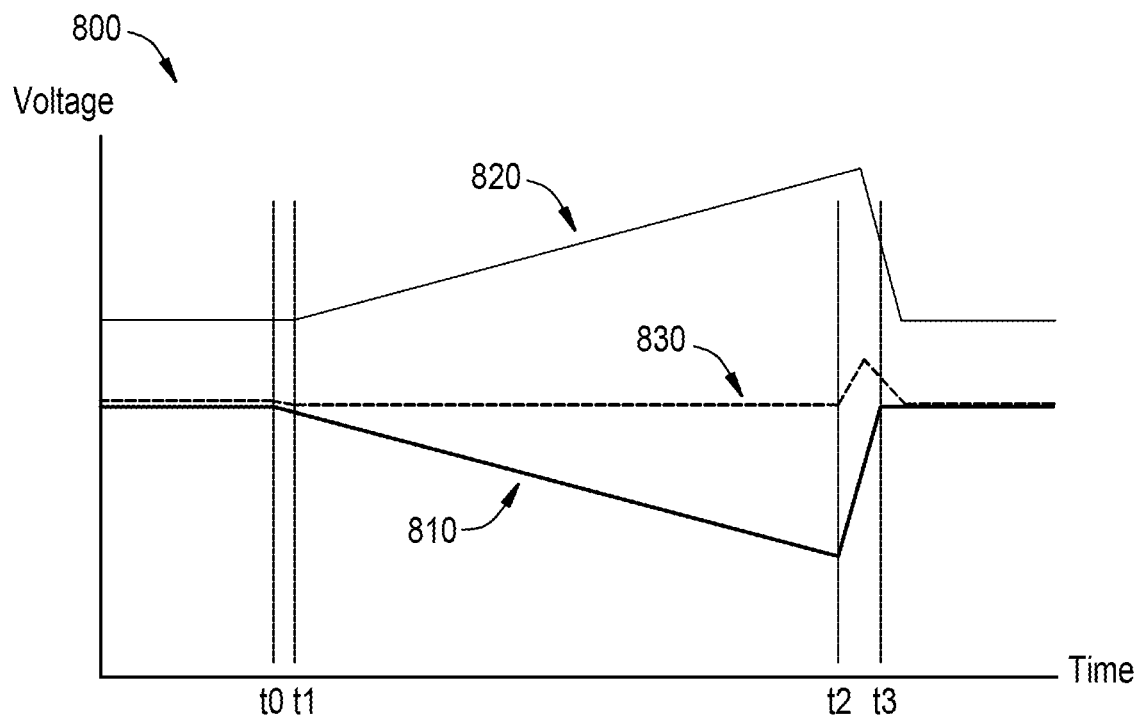
FIG. 11 illustrates an exemplary graph of voltage vs. time for a medical device.

In another example, the request data received by the RFID tag 625 can characterize a query for an operational parameter that corresponds to an error that is observed with the medical device 630 during an operation. FIG. 11 illustrates an exemplary graph 800 of voltage vs. time for a medical device (e.g. medical device 630 of FIG. 10). Using the example provided in FIG. 11, if it is observed that the device is indicating a voltage drop during operation, as indicated by the uncompensated voltage 810, the query can be directed toward a voltage operational parameter. In this case, responsive to the query, the smart package assembly 605 can be configured to determine and transmit corresponding executable code that, when run by the medical device 630 or another device configured to control the medical device 630 (e.g., a control module operably coupled to the medical device 630), is configured to compensate for the drop by using a compensation factor 820. This can increase the voltage that will reach a motor of the device 630, or the like, resulting in a compensated voltage 830.

In this case, as described above, the voltage operational parameter can be in the form of compressed executable code, or in the form of an electronic identifier, such as a unique series of bits that represent a link to the code file that is stored elsewhere (e.g. the internet).

As an illustrative example, code for the voltage operational parameter could look as follows:
//Set the desired voltage for firing the medical device
setpoint_voltage=5.0//in volts
//Read the actual voltage of the device
actual_voltage=read_voltage( )
//Calculate the error between the desired voltage and the actual voltage
error=setpoint_voltage−actual_voltage
//If the error is within a certain threshold, do nothing
if abs(error)<0.1:
  return
//Otherwise, adjust the voltage to correct the error
else:
//Calculate the amount of correction to apply based on the error
correction=Kp*error//Kp is a tuning constant
//Apply the correction to the device's firing voltage
new_voltage=actual_voltage+correction
set_voltage(new_voltage)

In some embodiments, the code described above could be compressed down to only the essential bits of information, without losing functionality. The compressed code could then be stored on the RFID tag 625 of the smart package assembly 605 and could be transmitted to the remote device 615, responsive to a request received from the remote device 615. As a further illustrative example, code described above could be compressed from 654 characters to 62 characters, as follows:
s=5.0;a=read( );e=s−a;
if abs(e)<0.1:return
else:k=0.1*e;set(k+a)

Further, as described above, the device 630 and/or the remote device 615 can be configured to transmit data regarding the other operating systems or devices being used with the device 630 in order to provide a context of the operating environment. As described above, this contextual data can include operational data, component data, manufacturer, etc. Additionally, the remote device 615 can be configured to transmit patient specific data to be used in combination with the other data stored on the memory of the package assembly 605 to determine the operational parameter that is necessary to transmit to the remote device 615. Patient specific data can include, for example a patient weight, age, previous conditions, etc. In the context of the example provided above, the assembly 605 can be configured to determine input values for the variables of the voltage operational parameter provided above based on the contextual data and patient specific data provided. The RFID tag 625 can be configured to transmit at 720 the compressed executable code that, when run by the device 630 or another device controlling the device 630, is configured to calibrate the device 630 for operation on the specific patient.

As described above, the data received by the RFID tag 625 from the medical device 630 at 705 can also include operational data of the medical device 630. The operational data can include a number of past and/or allowable activations of the medical device 630, or a component thereof, anomaly events recorded by the medical device 630 that might indicate abuse and/or damage, etc. In some embodiments, the operational data can be recorded by sensors in the medical device 630. For example, if the medical device 630 is a surgical stapler, sensors in the stapler (or connected to the stapler externally) that can track and record various metrics, such as the number of staples used, the amount of force applied, duration of use, etc. This data can be used to identify any instances of abuse or improper use, as well as to monitor the overall performance of the stapler. Other approaches to tracking operational data can include sensor-based monitoring systems in an operating room. These systems can track the movement and usage of the medical device, and provide real-time data on their use to the RFID tag 625. In some embodiments, operational data recorded by sensor-based monitoring systems in an operating room can be transmitted using RF communication, similarly to the data communicated at 705.

As discussed above, in some embodiments, the number of activations of the medical device 630 (e.g. the stapler of the example provided above) can be used as the operational data. In this case, the number of activations transmitted from the medical device 630 at 705 can be used by the RFID tag 625 of the smart package assembly 605 to determine a state of the device 630 prior to a next operation. In some embodiments, the RFID tag 625 of the smart package assembly 605 can be configured to compare the number of activations of the medical device 630 to a maximum number of activations for the device 630 stored in the plurality of subsets (e.g. 650A-650B) to determine whether or not the device 630 has been abused and/or requires maintenance. Upon receipt of the smart package assembly 605 in the operating room, responsive to a request at 715, the RFID tag 625 of the smart package assembly 605 can be configured to transmit the operational data to the remote device 615 at 720.

In some embodiments, the response data transmitted at 720 can further include instructional data and/or executable code to be used by the remote device 615, or directly by another medical device in combination with operational data. For example, the request data can characterize a query for the reusability and/or harvestability of the medical device 630, or components thereof. In this case, the operational data transmitted at 720 can include a number of past and/or allowable activations of the device 630, a previous maintenance log of the device 630, etc. In the event that maintenance is required, the response data could also include informational data including, but not limited to, a compressed training video, that when decompressed by the remote device 615, can be played to teach a user how to perform a maintenance or replacement procedure on the device 630. In some embodiments, harvestability can be determined by using a variety of transducers disposed within the medical device 630 and/or the package assembly 605.

In some embodiments, the operational data of the medical device 630 can be stored in a compressed form of error codes. In this case, as described above, all other "unimportant" data can be disregarded, and only anomaly events such as errors, failures, potential abuse, etc. can be recorded. In some embodiments, the error codes can be simple electronic identifiers that can be used to represent errors, failures, and abuse, respectively, in a way that can be understood by the remote device 615. The use of error codes can also aid in categorizing the compressed operational data into different types of errors so that a more targeted acquisition of error data can be made by the remote device 615. In some embodiments, the error codes can be stored on a separate tag within the assembly 605. In this case, the separate tag can be similar to the RFID tag 625, but specifically used for storing error codes. This can be useful if the error code needs to be independent of the data stored on the main package tag 625.

As discussed above, in some embodiments, the smart package assembly 605 can be a return package configured to return the medical device 630, or a component thereof, to the manufacturer. In this case, the flow of data described above can be reversed. For example, in reference to the example provided above, the stapler can be used during an operation and then placed back into the smart package assembly 605 for return. In this case, the remote device can be configured to transmit operational data from the most recent operation to the RFID tag 625 at 730. The operational data transferred at 730 can include, but is not limited to a surgeon report of the operation, and operational data tracked by devices and systems used in the operation. In some embodiments, this data can be compressed similarly to as described above. Similarly, in some embodiments, the medical device 630 can be configured to transmit operational data from the most recent operation to the RFID tag 625 at 735. In some embodiments, the data transferred at 735 can be structurally similar to the data transferred at 705. The data transmitted at 730 by the remote device 615 and the data transmitted by the medical device at 735 can be stored in the memory 650 of the RFID tag 625 and can be analyzed by the manufacturer upon receipt of the return package.

For example, in the event that a surgeon reports a failure with the surgical stapler, the remote device 615 can be configured transmit that report to the RFID tag 625 at 730. The operational data that is transmitted at 730 can be used by the manufacturer to investigate the failure. In some embodiments, the medical device 630 can also be configured to transmit operational data tracked by the medical device 630 during the operation at 735. The data transmitted at 730 and at 735 can be cross-referenced by the manufacturer to ensure that no discrepancies exist.

For example, if the surgeon indicates in the data transmitted at 730 that a component of the stapler was broken during the shipping process or has a manufacturing defect, the operational data transmitted at 735 can be used to validate/invalidate that claim. If, for example, a component of the stapler is broken, but no anomaly event was reported from one or more sensors configured to monitor the component, then it can be determined that the component was in fact broken during the shipping process or has a manufacturing defect. Alternatively, for example, if the component is broken, and data characterizing activations of the stapler when the stapler was checked in for surgery overlaps with data characterizing an anomaly event, then it can be determined that the component was broken during a surgical operation. In the event that it is determined that the component was broken during surgery, the operational data can be investigated further to identify how the damage occurred.

Figure 12:
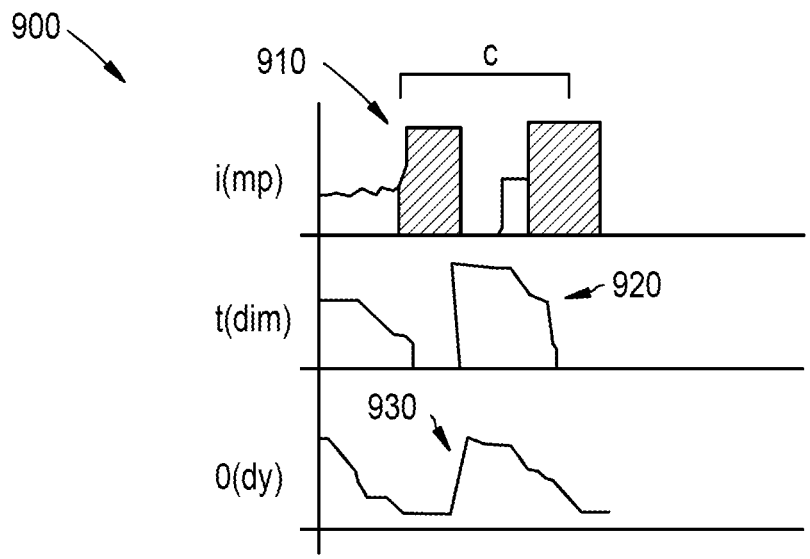
FIG. 12 illustrates an exemplary graph of voltage vs. time for a medical device.

In another example, the surgeon may indicate in the data transmitted at 730 that a component of the stapler was broken during the operation due to a defect. In this case, the operational data transmitted at 735 can also be used to validate/invalidate that claim. For example, FIG. 12 is an exemplary graph 900 illustrating a series of plots including a current vs. time plot 910, a temperature vs. time plot 920, and a phase vs. time plot 930. In some embodiments, the series of plots, or a compressed version thereof, or an electronic identifier corresponding to the series of plots can be transmitted to the RFID tag 625 of the smart package assembly 605 at 735 (in reference to FIG. 11). In some embodiments, the exemplary graph 900, or the like, can be analyzed by the manufacturer, in combination with the surgeon report transmitted at 730 (in reference to FIG. 11) to determine whether the component of the stapler was broken due to a defect, or due to a user error on behalf of the surgeon.

For example, the current plot 910 can indicate that the surgeon fired the device X amount of times in Y period of time. Additionally, the temperature plot 920 can be analyzed to indicate that the temperature of the stapler rose above Z degrees. These variables can be cross-referenced with predetermined maximum threshold values for each variable, to determine if the stapler was abused during the operation.

In another example, the operational data transmitted at 730 and/or 735 can include data specifically regarding previous geographical locations of use, previous times of use, previous durations of use, etc. In this case the operational data received by the RFID tag 625 of the smart package assembly 605 at 730 and/or 735 can be analyzed by the manufacturer to determine whether or not the medical device 630 has been tampered with or if it is a counterfeit.

Further, in response to receiving the request data at 715, the processor 645 of the RFID tag 625 can use the request data and/or instructions stored on the memory 650 (e.g., one or more data transfer rules) of the RFID tag 625 to determine response data that it will transmit to the remote device 615, at 720. The response data can be transmitted from the RFID tag 625 to the remote device 615. The remote device 615 can, at 725, transmit the response data to the remote network 610 for further processing by other electronic components in operable communication with the remote network 610. For example, in the event that the request data includes a query for a specific electronic identifier, the response data can include the requested electronic identifier along with corresponding compressed data. The remote device 615 can use this electronic identifier to determine the type of data being transmitted and then decode the compressed data appropriately.

In some cases, the medical device 630 or a component thereof may be being used in an unauthorized environment, or with an unauthorized device. Accordingly, in some embodiments, the remote device 615 and or the remote network 610 can have a video feed or other means of tracking what devices are being used with the medical device 630. In the event that a device is unrecognized, or unauthorized, the remote device 615 can be configured to transmit a notification, at 725, to the remote network to notify an interested party of potential misuse. Additionally, in the event that the smart package assembly 605 is a return package, the data transmitted at 730 can include the notification described above.

There are several technical advantages of a smart package assembly that is capable of providing automatic, selective transmission of executable code with a requesting system. Technical advantages can include configuration simplification, reduced training requirements, and increased flexibility.

The transference of selective executable code based on the specific medical device, and a host operating system/device can be advantageous, as it allows for a simplified configuration process. Specifically, providing customized executable code to a host operating system/device, directly from the medical device's packaging, the systems described herein can eliminate the need for manual configuration, or unnecessary returns. In a case where the operating system/device is not properly configured/updated for use with the medical device, the systems described herein can automatically ensure that the operating system and/or other devices are properly configured for use with the medical device by using data stored directly on the medical device's packaging. This ability can also help reduce the risk of errors and malfunctions that can result from using incompatible or outdated software on a host operating system/device.

Additionally, the systems described herein allow for reduced training requirements on behalf of medical device operators (e.g., surgeons, nurses, etc.). By automating the setup process that comes with using a new medical device, the smart package assembly provided can help reduce the amount of training that healthcare providers and other users need to use the medical device. This can help reduce the overall cost of training and increase the speed at which users can become proficient in using the device.

Further, the systems described herein advantageously allow for increased flexibility in the use of the medical device stored within the smart package assembly provided. The smart package assembly can be configured to store a variety of executable code to be used for configuring a variety of host operating systems/devices. Accordingly, the smart package assembly provided can transmit executable code that is tailored to the specific host operating system/device that is being used for an operation with the medical device. Furthermore, the executable code that is transmitted by the smart package assembly can be tailored to a specific user (e.g., surgeon, nurse, etc.) and/or can be tailored to a specific patient, thus providing an additional layer of flexibility.

Certain illustrative implementations have been described to provide an overall understanding of the principles of the structure, function, manufacture, and use of the systems, devices, and methods disclosed herein. One or more examples of these implementations have been illustrated in the accompanying drawings. Those skilled in the art will understand that the systems, devices, and methods specifically described herein and illustrated in the accompanying drawings are non-limiting illustrative implementations and that the scope of the present invention is defined solely by the claims. The features illustrated or described in connection with one illustrative implementation may be combined with the features of other implementations. Such modifications and variations are intended to be included within the scope of the present invention. Further, in the present disclosure, like-named components of the implementations generally have similar features, and thus within a particular implementation each feature of each like-named component is not necessarily fully elaborated upon.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

One skilled in the art will appreciate further features and advantages of the invention based on the above-described implementations. Accordingly, the present application is not to be limited by what has been particularly shown and described, except as indicated by the appended claims. All publications and references cited herein are expressly incorporated by reference in their entirety.

The invention claimed is:

1. An assembly, comprising:
 a medical device;
 a protective container having the medical device disposed therein, the protective container being sealed to prevent contaminates from contacting the medical device; and
 a radiofrequency identification (RFID) tag disposed within the protective container, the RFID tag including a data processor and memory storing first data and instructions configured to cause the data processor to perform operations comprising:
  receiving request data from a remote network in operable communication with the RFID tag, the request data characterizing a future data processing operation to be performed on a subset of the first data after the subset is transmitted from the RFID tag and a request for the subset of the first data to be transmitted from the RFID tag to the remote network,
  determining, based on the received request data, the subset of the first data to be provided to the remote network, and
  providing the determined subset of the first data to the remote network.

2. The assembly of claim 1, wherein the request data received from the remote network includes location data relating to a location of the remote network, and wherein the subset of the first data is determined based on the location data received from the remote network.

3. The assembly of claim 1, wherein the operations further comprise:
receiving, from the medical device, device data characterizing a history of use of the medical device and a listing of reusable components of the medical device,
writing the received device data to the memory of the RFID tag such that the device use data is included in the first data,
determining reusable component data characterizing the listing of the reusable components of the medical device, and
determining whether the at least one data processor is in operable communication with the remote network,
wherein the determined subset of the first data includes the reusable component data when at least one data processor is determined to be in operable communication with the remote network.

4. The assembly of claim 3, wherein the operations further comprise:
receiving, from the remote network, procedure query data characterizing a request to determine whether the medical device has been used in a surgical procedure,
determining, based on the received device data and in response to receiving the procedure query data, whether the medical device has been used in a surgical procedure,
in response to determining that the medical device has been used in a surgical procedure, providing the device data to the remote network.

5. The assembly of claim 1, wherein the operations further comprise:
receiving, from the remote network, defect data characterizing a defect of the medical device, and
writing the defect data to the memory of the RFID tag such that the defect data is included in the first data.

6. The assembly of claim 1, wherein the operations further comprise:
determining at least one component of the remote network configured to receive the determined subset of the first data and to transmit the determined subset of the first data to a recipient server in operable communication with the remote network, and
wherein the providing includes:
transmitting the determined subset of the first data to the at least one component, and
transmitting, to the at least one component, instructions configured to cause the at least one component to transmit the determined subset of the first data to the recipient server.

7. An assembly, comprising:
a medical device;
a protective container having the medical device disposed therein, the protective container being sealed to prevent contaminates from contacting the medical device; and
a radiofrequency identification (RFID) tag disposed within the protective container, the RFID tag including a data processor and memory storing first data and instructions configured to cause the data processor to perform operations comprising:
receiving request data from a remote network in operable communication with the RFID tag, the request data characterizing a location of the remote network and a request for a subset of the first data to be transmitted from the RFID tag to the remote network,
determining, based on the received request data, the subset of the first data to be provided to the remote network, and
providing the determined subset of the first data to the remote network.

8. The assembly of claim 7, wherein the request data received from the remote network characterizes a future data processing operation to be performed on a subset of the first data after the subset is transmitted from the RFID tag, and wherein the subset of the first data is determined based on the future data processing operation characterized by the received request data.

9. The assembly of claim 7, wherein the operations further comprise:
receiving, from the medical device, device data characterizing a history of use of the medical device and a listing of reusable components of the medical device,
writing the received device data to the memory of the RFID tag such that the device use data is included in the first data,
determining reusable component data characterizing the listing of the reusable components of the medical device, and
determining whether the at least one data processor is in operable communication with the remote network,
wherein the determined subset of the first data includes the reusable component data when at least one data processor is determined to be in operable communication with the remote network.

10. The assembly of claim 9, wherein the operations further comprise:
receiving, from the remote network, procedure query data characterizing a request to determine whether the medical device has been used in a surgical procedure,
determining, based on the received device data and in response to receiving the procedure query data, whether the medical device has been used in a surgical procedure,
in response to determining that the medical device has been used in a surgical procedure, providing the device data to the remote network.

11. The assembly of claim 7, wherein the operations further comprise:
receiving, from the remote network, defect data characterizing a defect of the medical device, and
writing the defect data to the memory of the RFID tag such that the defect data is included in the first data.

12. The assembly of claim 7, wherein the operations further comprise:
determining at least one component of the remote network configured to receive the determined subset of the first data and to transmit the determined subset of the first data to a recipient server in operable communication with the remote network, and
wherein the providing includes:
transmitting the determined subset of the first data to the at least one component, and
transmitting, to the at least one component, instructions configured to cause the at least one component to transmit the determined subset of the first data to the recipient server.

13. A system, comprising:
an RFID tag;
at least one data processor communicatively coupled to the RFID tag; and
memory storing first data and instructions configured to cause the at least one data processor to perform operations comprising:
receiving request data from a remote network in operable communication with the RFID tag, the request data characterizing at least one of a location of the remote network and a future data processing operation to be performed on a subset of the first data after the subset is transmitted from the RFID tag, the request data further characterizing a request for a subset of the first data to be transmitted from the RFID tag to the remote network,
determining, based on the received request data, the subset of the first data to be provided to the remote network, and
providing the determined subset of the first data to the remote network.

14. The system of claim 13, wherein the operations further comprise:
receiving, from a medical device associated with the RFID tag, device data characterizing a history of use of the medical device and a listing of reusable components of the medical device,
writing the received device data to the memory such that the device use data is included in the first data,
determining reusable component data characterizing the listing of the reusable components of the medical device, and
determining whether the at least one data processor is in operable communication with the remote network,
wherein the determined subset of the first data includes the reusable component data when at least one data processor is determined to be in operable communication with the remote network.

15. The system of claim 14, wherein the operations further comprise:
receiving, from the remote network, procedure query data characterizing a request to determine whether the medical device has been used in a surgical procedure,
determining, based on the received device data and in response to receiving the procedure query data, whether the medical device has been used in a surgical procedure,
in response to determining that the medical device has been used in a surgical procedure, providing the device data to the remote network.

16. The system of claim 13, wherein the operations further comprise:
receiving, from the remote network, defect data characterizing a defect of the medical device, and
writing the defect data to the memory such that the defect data is included in the first data.

17. The system of claim 13, wherein the operations further comprise:
determining at least one component of the remote network configured to receive the determined subset of the first data and to transmit the determined subset of the first data to a recipient server in operable communication with the remote network, and
wherein the providing includes:
transmitting the determined subset of the first data to the at least one component, and
transmitting, to the at least one component, instructions configured to cause the at least one component to transmit the determined subset of the first data to the recipient server.

* * * * *